(12) United States Patent
Snow et al.

(10) Patent No.: US 8,986,362 B2
(45) Date of Patent: Mar. 24, 2015

(54) DEVICES AND METHODS FOR CONTROLLING EXPANDABLE PROSTHESES DURING DEPLOYMENT

(75) Inventors: David W. Snow, San Carlos, CA (US);
Joseph Karratt, Millbrae, CA (US);
Jeffry J. Grainger, Portola Valley, CA (US); Denise Demarais, San Jose, CA (US)

(73) Assignee: J.W. Medical Systems Ltd., Palo Alto, CA (US)

( * ) Notice: Subject to any disclaimer, the term of this patent is extended or adjusted under 35 U.S.C. 154(b) by 0 days.

(21) Appl. No.: 12/471,064

(22) Filed: May 22, 2009

(65) Prior Publication Data
US 2009/0234428 A1      Sep. 17, 2009

Related U.S. Application Data

(63) Continuation of application No. 10/957,079, filed on Sep. 30, 2004, now abandoned, which is a continuation-in-part of application No. 10/879,949, filed on Jun. 28, 2004, now abandoned.

(51) Int. Cl.
*A61F 2/06*        (2013.01)
*A61F 2/966*      (2013.01)
(Continued)

(52) U.S. Cl.
CPC . *A61F 2/966* (2013.01); *A61F 2/95* (2013.01); *A61F 2/97* (2013.01); *A61F 2/958* (2013.01);
(Continued)

(58) Field of Classification Search
USPC .............. 623/1.11, 1.12, 1.15, 1.23; 606/108, 606/200
See application file for complete search history.

(56) References Cited

U.S. PATENT DOCUMENTS 4,069,825 A    1/1978 Akiyama
4,468,224 A    8/1984 Enzmann et al.
(Continued)

FOREIGN PATENT DOCUMENTS

CN     1856280 A      11/2006
DE     1 953 1659       3/1997
(Continued)

OTHER PUBLICATIONS

Colombo, "The Invatec Bifurcation Stent Solution" Bifurcation Stents: Novel Solutions, TCT 2003, Washington: Sep. 15-19, 2003, 24 pages total.

(Continued)

*Primary Examiner* — Victor Nguyen
*Assistant Examiner* — Kevin Everage
(74) *Attorney, Agent, or Firm* — Kilpatrick Townsend & Stockton LLP

(57) ABSTRACT

Prosthesis delivery devices and methods are provided that enable precise control of prosthesis position during deployment. The prosthesis delivery devices may carry multiple prostheses and include deployment mechanisms for delivery of a selectable number of prostheses. Control mechanisms are provided in the prosthesis delivery devices that control either or both of the axial and rotational positions of the prostheses during deployment. This enables the deployment of multiple prostheses at a target site with precision and predictability, eliminating excessive spacing or overlap between prostheses. In particular embodiments, the prostheses of the invention are deployed in stenotic lesions in coronary or peripheral arteries, or in other vascular locations.

20 Claims, 20 Drawing Sheets

(51) Int. Cl.
*A61F 2/95* (2013.01)
*A61F 2/97* (2013.01)
*A61F 2/958* (2013.01)
*A61F 2/82* (2013.01)

(52) U.S. Cl.
CPC ... *A61F 2002/826* (2013.01); *A61F 2002/9505* (2013.01); *A61F 2002/9511* (2013.01); *A61F 2002/9583* (2013.01); *A61F 2002/9665* (2013.01)
USPC ......... 623/1.11; 623/1.12; 623/1.23; 606/108

(56) References Cited

U.S. PATENT DOCUMENTS

| | | |
|---|---|---|
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,950,227 A | 8/1990 | Savin et al. |
| 4,988,356 A | 1/1991 | Crittenden et al. |
| 4,994,066 A | 2/1991 | Voss |
| 4,994,069 A | 2/1991 | Ritchart et al. |
| 4,994,298 A | 2/1991 | Yasuda |
| 5,013,318 A | 5/1991 | Spranza, III |
| 5,035,706 A | 7/1991 | Giantureo et al. |
| 5,040,548 A | 8/1991 | Yock |
| 5,061,273 A | 10/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,158,548 A | 10/1992 | Lau et al. |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,261,887 A | 11/1993 | Walker |
| 5,273,536 A | 12/1993 | Savas |
| 5,282,823 A | 2/1994 | Schwartz et al. |
| 5,282,824 A | 2/1994 | Gianturco |
| 5,300,085 A | 4/1994 | Yock |
| 5,312,415 A | 5/1994 | Palermo |
| 5,328,469 A | 7/1994 | Coletti |
| 5,334,187 A | 8/1994 | Fischell et al. |
| 5,391,172 A | 2/1995 | Williams et al. |
| 5,421,955 A | 6/1995 | Lau et al. |
| 5,443,498 A | 8/1995 | Fontaine |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,484,444 A | 1/1996 | Braunschweiler et al. |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,522,882 A | 6/1996 | Gaterud et al. |
| 5,527,354 A | 6/1996 | Fontaine et al. |
| 5,531,735 A | 7/1996 | Thompson |
| 5,533,968 A | 7/1996 | Muni et al. |
| 5,534,007 A | 7/1996 | St. Germain et al. |
| 5,545,209 A | 8/1996 | Roberts et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,591,195 A | 1/1997 | Taheri et al. |
| 5,593,412 A | 1/1997 | Martinez et al. |
| 5,607,444 A | 3/1997 | Lam |
| 5,607,463 A | 3/1997 | Schwartz et al. |
| 5,628,755 A | 5/1997 | Heller et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Polanskyj Stockert et al. |
| 5,662,703 A | 9/1997 | Yurek et al. |
| 5,670,161 A | 9/1997 | Healy et al. |
| 5,676,654 A | 10/1997 | Ellis et al. |
| 5,683,451 A | 11/1997 | Lenker et al. |
| 5,690,644 A | 11/1997 | Yurek et al. |
| 5,693,085 A | 12/1997 | Buirge et al. |
| 5,697,948 A | 12/1997 | Marin et al. |
| 5,697,971 A | 12/1997 | Fischell et al. |
| 5,702,418 A | 12/1997 | Ravenscroft |
| 5,702,419 A | 12/1997 | Berry et al. |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,890 A | 5/1998 | Shaknovich |
| 5,749,921 A | 5/1998 | Lenker et al. |
| 5,755,697 A | 5/1998 | Jones et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,792,144 A | 8/1998 | Fischell et al. |
| 5,797,951 A | 8/1998 | Mueller et al. |
| 5,800,519 A | 9/1998 | Sandock |
| 5,807,398 A | 9/1998 | Shaknovich |
| 5,824,040 A | 10/1998 | Cox et al. |
| 5,824,041 A * | 10/1998 | Lenker et al. .................. 606/195 |
| 5,833,694 A * | 11/1998 | Poncet .......................... 623/1.11 |
| 5,836,964 A | 11/1998 | Richter et al. |
| 5,843,090 A | 12/1998 | Schuetz |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,921,971 A | 7/1999 | Agro et al. |
| 5,922,020 A | 7/1999 | Klein et al. |
| 5,941,869 A | 8/1999 | Patterson et al. |
| 5,951,585 A | 9/1999 | Cathcart et al. |
| 5,961,536 A | 10/1999 | Mickley et al. |
| 5,965,879 A | 10/1999 | Leviton |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |

(56) References Cited

U.S. PATENT DOCUMENTS

| | | | |
|---|---|---|---|
| 5,980,514 A | 11/1999 | Kupiecki et al. | |
| 5,980,552 A | 11/1999 | Pinchasik et al. | |
| 5,984,957 A | 11/1999 | Laptewicz, Jr. et al. | |
| 5,989,280 A | 11/1999 | Euteneuer et al. | |
| 5,993,484 A | 11/1999 | Shmulewitz | |
| 5,997,563 A | 12/1999 | Kretzers et al. | |
| 6,004,328 A | 12/1999 | Solar | |
| 6,007,517 A | 12/1999 | Anderson | |
| 6,010,530 A | 1/2000 | Goicoechea | |
| 6,022,359 A | 2/2000 | Frantzen | |
| 6,022,374 A | 2/2000 | Imran | |
| 6,027,519 A | 2/2000 | Stanford | |
| 6,033,434 A | 3/2000 | Borghi | |
| 6,036,725 A | 3/2000 | Avellanet | |
| 6,039,721 A | 3/2000 | Johnson et al. | |
| 6,042,589 A | 3/2000 | Marianne | |
| 6,050,999 A | 4/2000 | Paraschac et al. | |
| 6,056,722 A | 5/2000 | Jayaraman | |
| 6,063,111 A | 5/2000 | Hieshima et al. | |
| 6,066,155 A | 5/2000 | Amann et al. | |
| 6,068,655 A | 5/2000 | Seguin et al. | |
| 6,070,589 A | 6/2000 | Keith et al. | |
| 6,090,063 A | 7/2000 | Makower et al. | |
| 6,090,136 A | 7/2000 | McDonald et al. | |
| 6,102,942 A | 8/2000 | Ahari | |
| 6,106,530 A | 8/2000 | Harada | |
| RE36,857 E | 9/2000 | Euteneuer et al. | |
| 6,120,477 A | 9/2000 | Campbell et al. | |
| 6,120,522 A * | 9/2000 | Vrba et al. | 606/190 |
| 6,123,712 A | 9/2000 | Di Caprio et al. | |
| 6,123,723 A | 9/2000 | Konya et al. | |
| 6,126,685 A | 10/2000 | Lenker et al. | |
| 6,129,756 A | 10/2000 | Kugler | |
| 6,132,460 A | 10/2000 | Thompson | |
| 6,139,572 A | 10/2000 | Campbell et al. | |
| 6,143,016 A | 11/2000 | Bleam et al. | |
| 6,165,167 A | 12/2000 | Delaloye | |
| 6,165,210 A | 12/2000 | Lau et al. | |
| 6,171,334 B1 | 1/2001 | Cox | |
| 6,179,878 B1 | 1/2001 | Duerig | |
| 6,183,509 B1 | 2/2001 | Dibie | |
| 6,187,034 B1 | 2/2001 | Frantzen | |
| 6,190,402 B1 | 2/2001 | Horton et al. | |
| 6,196,995 B1 | 3/2001 | Fagan | |
| 6,200,337 B1 | 3/2001 | Moriuchi et al. | |
| 6,217,585 B1 | 4/2001 | Houser et al. | |
| 6,238,991 B1 | 5/2001 | Suzuki | |
| 6,241,691 B1 | 6/2001 | Ferrera et al. | |
| 6,241,758 B1 | 6/2001 | Cox | |
| 6,248,122 B1 | 6/2001 | Klumb et al. | |
| 6,251,132 B1 | 6/2001 | Ravenscroft et al. | |
| 6,251,134 B1 | 6/2001 | Alt et al. | |
| 6,254,612 B1 | 7/2001 | Hieshima | |
| 6,254,628 B1 | 7/2001 | Wallace et al. | |
| 6,258,117 B1 | 7/2001 | Camrud et al. | |
| 6,264,688 B1 | 7/2001 | Herklotz et al. | |
| 6,267,783 B1 | 7/2001 | Letendre et al. | |
| 6,270,524 B1 | 8/2001 | Kim | |
| 6,273,895 B1 | 8/2001 | Pinchuk et al. | |
| 6,273,911 B1 | 8/2001 | Cox et al. | |
| 6,273,913 B1 | 8/2001 | Wright et al. | |
| 6,287,291 B1 | 9/2001 | Bigus et al. | |
| 6,312,458 B1 | 11/2001 | Golds | |
| 6,315,794 B1 | 11/2001 | Richter | |
| 6,319,277 B1 | 11/2001 | Rudnick et al. | |
| 6,322,586 B1 | 11/2001 | Monroe et al. | |
| 6,325,823 B1 | 12/2001 | Horzewski et al. | |
| 6,334,871 B1 | 1/2002 | Dor et al. | |
| 6,340,366 B2 | 1/2002 | Wijay | |
| 6,344,272 B1 | 2/2002 | Oldenburg et al. | |
| 6,348,065 B1 | 2/2002 | Brown et al. | |
| 6,350,252 B2 | 2/2002 | Ray et al. | |
| 6,350,277 B1 | 2/2002 | Kocur | |
| 6,357,104 B1 | 3/2002 | Myers | |
| 6,361,558 B1 | 3/2002 | Hieshima et al. | |
| 6,375,676 B1 | 4/2002 | Cox | |
| 6,379,365 B1 | 4/2002 | Diaz | |
| 6,383,171 B1 | 5/2002 | Gifford et al. | |
| 6,394,995 B1 | 5/2002 | Solar et al. | |
| 6,409,753 B1 | 6/2002 | Brown et al. | |
| 6,415,696 B1 | 7/2002 | Erickeson et al. | |
| 6,416,543 B1 | 7/2002 | Hilaire et al. | |
| 6,419,693 B1 | 7/2002 | Fariabi | |
| 6,425,898 B1 | 7/2002 | Wilson et al. | |
| 6,428,811 B1 | 8/2002 | West et al. | |
| 6,451,025 B1 | 9/2002 | Jervis | |
| 6,451,050 B1 | 9/2002 | Rudakov et al. | |
| 6,464,720 B2 | 10/2002 | Boatman et al. | |
| 6,468,298 B1 | 10/2002 | Pelton | |
| 6,468,299 B2 | 10/2002 | Stack et al. | |
| 6,485,510 B1 | 11/2002 | Camrud et al. | |
| 6,488,694 B1 | 12/2002 | Lau et al. | |
| 6,488,702 B1 | 12/2002 | Besselink | |
| 6,511,468 B1 | 1/2003 | Cragg et al. | |
| 6,520,986 B2 | 2/2003 | Martin et al. | |
| 6,520,987 B1 | 2/2003 | Plante | |
| 6,527,789 B1 | 3/2003 | Lau et al. | |
| 6,527,799 B2 | 3/2003 | Shanley | |
| 6,530,944 B2 | 3/2003 | West et al. | |
| 6,540,777 B2 | 4/2003 | Stenzel | |
| 6,551,350 B1 | 4/2003 | Thornton et al. | |
| 6,555,157 B1 | 4/2003 | Hossainy | |
| 6,558,415 B2 | 5/2003 | Thompson | |
| 6,562,067 B2 | 5/2003 | Mathis | |
| 6,565,599 B1 | 5/2003 | Hong et al. | |
| 6,569,180 B1 | 5/2003 | Sirhan et al. | |
| 6,575,993 B1 | 6/2003 | Yock | |
| 6,579,305 B1 | 6/2003 | Lashinski | |
| 6,579,309 B1 | 6/2003 | Loos et al. | |
| 6,582,394 B1 | 6/2003 | Reiss et al. | |
| 6,582,460 B1 | 6/2003 | Cryer | |
| 6,585,756 B1 | 7/2003 | Strecker | |
| 6,589,273 B1 | 7/2003 | McDermott | |
| 6,592,549 B2 | 7/2003 | Gerdts et al. | |
| 6,599,296 B1 | 7/2003 | Gillick et al. | |
| 6,599,314 B2 | 7/2003 | Mathis | |
| 6,602,226 B1 | 8/2003 | Smith et al. | |
| 6,602,282 B1 | 8/2003 | Yan | |
| 6,605,062 B1 | 8/2003 | Hurley et al. | |
| 6,605,109 B2 | 8/2003 | Fiedler | |
| 6,607,553 B1 | 8/2003 | Healy et al. | |
| 6,613,074 B1 | 9/2003 | Mitelberg et al. | |
| 6,629,992 B2 | 10/2003 | Bigus et al. | |
| 6,645,517 B2 | 11/2003 | West | |
| 6,645,547 B1 | 11/2003 | Shekalim et al. | |
| 6,656,212 B2 | 12/2003 | Ravenscroft et al. | |
| 6,660,031 B2 | 12/2003 | Tran et al. | |
| 6,660,381 B2 | 12/2003 | Halas et al. | |
| 6,663,660 B2 | 12/2003 | Dusbabek et al. | |
| 6,666,883 B1 | 12/2003 | Seguin et al. | |
| 6,676,693 B1 * | 1/2004 | Belding et al. | 623/1.11 |
| 6,676,695 B1 | 1/2004 | Solem | |
| 6,679,909 B2 | 1/2004 | McIntosh et al. | |
| 6,685,730 B2 | 2/2004 | West et al. | |
| 6,692,465 B2 | 2/2004 | Kramer | |
| 6,699,280 B2 | 3/2004 | Camrud et al. | |
| 6,699,281 B2 | 3/2004 | Vallana et al. | |
| 6,699,724 B1 | 3/2004 | West et al. | |
| 6,702,843 B1 | 3/2004 | Brown | |
| 6,709,379 B1 | 3/2004 | Brandau et al. | |
| 6,709,440 B2 | 3/2004 | Callol et al. | |
| 6,712,827 B2 | 3/2004 | Ellis et al. | |
| 6,712,845 B2 | 3/2004 | Hossainy | |
| 6,723,071 B2 | 4/2004 | Gerdts et al. | |
| 6,736,842 B2 | 5/2004 | Healy et al. | |
| 6,743,219 B1 | 6/2004 | Dwyer et al. | |
| 6,743,251 B1 | 6/2004 | Eder | |
| 6,761,734 B2 | 7/2004 | Suhr | |
| 6,776,771 B2 | 8/2004 | van Moorlegem et al. | |
| 6,778,316 B2 | 8/2004 | Halas et al. | |
| 6,790,227 B2 | 9/2004 | Burgermeister | |
| 6,800,065 B2 | 10/2004 | Duane et al. | |
| 6,825,203 B2 | 11/2004 | Pasternak et al. | |
| 6,837,901 B2 | 1/2005 | Rabkin et al. | |

(56) References Cited

U.S. PATENT DOCUMENTS

| | | |
|---|---|---|
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,899,728 B1 | 5/2005 | Phillips et al. |
| 6,913,619 B2 | 7/2005 | Brown et al. |
| 6,918,928 B2 | 7/2005 | Wolinsky et al. |
| 6,939,376 B2 | 9/2005 | Shulz et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,004,964 B2 | 2/2006 | Thompson et al. |
| 7,005,454 B2 | 2/2006 | Brocchini et al. |
| 7,022,132 B2 | 4/2006 | Kocur |
| 7,029,493 B2 | 4/2006 | Majercak et al. |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,131,993 B2 | 11/2006 | Gregorich |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,169,174 B2 | 1/2007 | Fischell et al. |
| 7,172,620 B2 | 2/2007 | Gilson |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,208,002 B2 | 4/2007 | Shelso |
| 7,220,275 B2 | 5/2007 | Davidson et al. |
| 7,220,755 B2 | 5/2007 | Betts et al. |
| 7,223,283 B2 | 5/2007 | Chouinard |
| 7,238,197 B2 | 7/2007 | Sequin et al. |
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |
| 7,402,168 B2 | 7/2008 | Sanderson et al. |
| 7,534,449 B2 | 5/2009 | Saltzman et al. |
| 7,699,886 B2 | 4/2010 | Sugimoto |
| 7,824,439 B2 | 11/2010 | Toyokawa |
| 7,892,273 B2 | 2/2011 | George et al. |
| 7,918,881 B2 | 4/2011 | Andreas et al. |
| 7,938,851 B2 | 5/2011 | Olson et al. |
| 7,993,388 B2 | 8/2011 | Lee et al. |
| 8,070,794 B2 | 12/2011 | Issenmann |
| 8,157,851 B2 | 4/2012 | Andreas |
| 8,282,680 B2 | 10/2012 | Kao et al. |
| 8,317,850 B2 | 11/2012 | Kusleika |
| 2001/0001824 A1 | 5/2001 | Wu |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2001/0049549 A1 | 12/2001 | Boylan et al. |
| 2002/0007212 A1 | 1/2002 | Brown et al. |
| 2002/0032457 A1 | 3/2002 | Sirhan et al. |
| 2002/0035395 A1 | 3/2002 | Sugimoto |
| 2002/0037358 A1 | 3/2002 | Barry et al. |
| 2002/0045914 A1 | 4/2002 | Roberts et al. |
| 2002/0052642 A1 | 5/2002 | Cox et al. |
| 2002/0087186 A1 | 7/2002 | Shelso |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0123792 A1 | 9/2002 | Burgermeister |
| 2002/0128706 A1 | 9/2002 | Osypka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0165599 A1 | 11/2002 | Nasralla |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0013266 A1 | 1/2003 | Fukuda et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0105511 A1 | 6/2003 | Welsh et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0163155 A1 | 8/2003 | Haverkost et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0073290 A1 | 4/2004 | Chouinard |
| 2004/0087965 A1 | 5/2004 | Levine et al. |
| 2004/0088044 A1 | 5/2004 | Brown et al. |
| 2004/0093061 A1 | 5/2004 | Acosta et al. |
| 2004/0093067 A1 | 5/2004 | Israel |
| 2004/0093077 A1 | 5/2004 | White et al. |
| 2004/0098081 A1 | 5/2004 | Landreville et al. |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0138737 A1 | 7/2004 | Davidson et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0215331 A1 | 10/2004 | Chew et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2004/0249435 A1 | 12/2004 | Andreas et al. |
| 2004/0249439 A1 | 12/2004 | Richter et al. |

(56) References Cited

U.S. PATENT DOCUMENTS

| | | |
|---|---|---|
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0055077 A1 | 3/2005 | Marco et al. |
| 2005/0075716 A1 | 4/2005 | Yan |
| 2005/0080474 A1 | 4/2005 | Andreas et al. |
| 2005/0080475 A1 | 4/2005 | Andreas et al. |
| 2005/0085897 A1 | 4/2005 | Bonsignore |
| 2005/0090846 A1 | 4/2005 | Pedersen et al. |
| 2005/0101624 A1 | 5/2005 | Betts et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0133164 A1 | 6/2005 | Fischer et al. |
| 2005/0137622 A1 | 6/2005 | Griffin |
| 2005/0143827 A1 | 6/2005 | Globerman et al. |
| 2005/0149159 A1 | 7/2005 | Andreas et al. |
| 2005/0149168 A1 | 7/2005 | Gregorich |
| 2005/0165378 A1 | 7/2005 | Heinrich et al. |
| 2005/0171568 A1 | 8/2005 | Duffy |
| 2005/0182477 A1 | 8/2005 | White |
| 2005/0209674 A1 | 9/2005 | Kutscher et al. |
| 2005/0209676 A1 | 9/2005 | Kusleika |
| 2005/0209680 A1 | 9/2005 | Gale et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1 | 12/2005 | Peckham |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0177476 A1 | 8/2006 | Saffran |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0125850 A1 | 5/2008 | Andreas et al. |
| 2008/0132989 A1 | 6/2008 | Snow et al. |
| 2008/0147162 A1 | 6/2008 | Andreas et al. |
| 2008/0177369 A1 | 7/2008 | Will et al. |
| 2008/0199510 A1 | 8/2008 | Ruane et al. |
| 2008/0208311 A1 | 8/2008 | Kao et al. |
| 2008/0208318 A1 | 8/2008 | Kao et al. |
| 2008/0234795 A1 | 9/2008 | Snow et al. |
| 2008/0234798 A1 | 9/2008 | Chew et al. |
| 2008/0234799 A1 | 9/2008 | Acosta et al. |
| 2008/0243225 A1 | 10/2008 | Satasiya et al. |
| 2008/0249607 A1 | 10/2008 | Webster et al. |
| 2008/0269865 A1 | 10/2008 | Snow et al. |
| 2009/0076584 A1 | 3/2009 | Mao et al. |
| 2009/0105686 A1 | 4/2009 | Snow et al. |
| 2009/0149863 A1 | 6/2009 | Andreas et al. |
| 2009/0228088 A1 | 9/2009 | Lowe et al. |
| 2009/0248137 A1 | 10/2009 | Andersen et al. |
| 2009/0248140 A1 | 10/2009 | Gerberding |
| 2009/0264979 A1 | 10/2009 | Kao et al. |
| 2009/0276030 A1 | 11/2009 | Kusleika |
| 2010/0004729 A1 | 1/2010 | Chew et al. |
| 2011/0022148 A1 | 1/2011 | Ruane et al. |
| 2011/0093056 A1 | 4/2011 | Kaplan et al. |
| 2011/0125248 A1 | 5/2011 | George et al. |
| 2011/0152996 A1 | 6/2011 | Snow et al. |
| 2013/0060321 A1 | 3/2013 | Kao et al. |
| 2013/0211494 A1 | 8/2013 | Snow et al. |
| 2014/0018899 A1 | 1/2014 | Snow et al. |

FOREIGN PATENT DOCUMENTS

| | | |
|---|---|---|
| DE | 1 963 0469 | 1/1998 |
| DE | 199 50 756 | 8/2000 |
| DE | 101 03 000 | 8/2002 |
| EP | 0 203 945 B2 | 12/1986 |
| EP | 0 274 129 B1 | 7/1988 |
| EP | 0 282 143 | 9/1988 |
| EP | 0 364 787 A1 | 4/1990 |
| EP | 0 505 686 | 9/1992 |
| EP | 0 533 960 | 3/1993 |
| EP | 0 596 145 | 5/1994 |
| EP | 0 696 447 A2 | 2/1996 |
| EP | 0 714 640 | 6/1996 |
| EP | 0 797 963 A2 | 1/1997 |
| EP | 0 947 180 | 10/1999 |
| EP | 1 254 644 A1 | 11/2002 |
| EP | 1 258 230 | 11/2002 |
| EP | 1 266 638 B1 | 12/2002 |
| EP | 1 277 449 | 1/2003 |
| EP | 1 290 987 A2 | 3/2003 |
| EP | 1 318 765 | 6/2003 |
| EP | 1 470 834 | 10/2004 |
| EP | 1 523 959 A2 | 4/2005 |
| EP | 1 523 960 A2 | 4/2005 |
| EP | 1 743 603 A2 | 1/2007 |
| GB | 2277875 A | 11/1994 |
| JP | 03-133446 | 6/1991 |
| JP | 07-132148 | 5/1995 |
| JP | 10-503663 | 4/1998 |
| JP | 10-295823 | 11/1998 |
| JP | 11-503056 T | 3/1999 |
| JP | 2935561 B2 | 8/1999 |
| JP | 2001-190687 | 7/2001 |
| JP | 2002-538932 T | 11/2002 |
| JP | 2004-121343 A | 4/2004 |
| WO | WO 94/27667 A1 | 12/1994 |
| WO | WO 95/26695 A2 | 10/1995 |
| WO | WO 95/29647 A2 | 11/1995 |
| WO | WO 96/26689 | 9/1996 |
| WO | WO 96/33677 | 10/1996 |
| WO | WO 96/37167 A1 | 11/1996 |
| WO | WO 96/39077 | 12/1996 |
| WO | WO 97/10778 | 3/1997 |
| WO | WO 97/46174 | 12/1997 |

(56) References Cited

FOREIGN PATENT DOCUMENTS

| WO | WO 97/48351 | 12/1997 |
|---|---|---|
| WO | WO 98/20810 | 5/1998 |
| WO | WO 98/37833 | 9/1998 |
| WO | WO 98/58600 | 12/1998 |
| WO | WO 99/01087 | 1/1999 |
| WO | WO 99/65421 | 12/1999 |
| WO | WO 00/12832 A3 | 3/2000 |
| WO | WO 00/15151 | 3/2000 |
| WO | WO 00/25841 | 5/2000 |
| WO | WO 00/32136 | 6/2000 |
| WO | WO 00/41649 | 7/2000 |
| WO | WO 00/50116 | 8/2000 |
| WO | WO 00/51525 A1 | 9/2000 |
| WO | WO 00/56237 | 9/2000 |
| WO | WO 00/62708 | 10/2000 |
| WO | WO 00/72780 | 12/2000 |
| WO | WO 01/26707 | 4/2001 |
| WO | WO 01/34063 | 5/2001 |
| WO | WO 01/70297 | 9/2001 |
| WO | WO 01/91918 | 12/2001 |
| WO | 02/060344 | 8/2002 |
| WO | 02/071975 | 9/2002 |
| WO | WO 02/085253 | 10/2002 |
| WO | WO 02/098326 | 12/2002 |
| WO | WO 03/022178 | 3/2003 |
| WO | WO 03/047651 | 6/2003 |
| WO | WO 03/051425 | 6/2003 |
| WO | WO 03/075797 | 9/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 A2 | 6/2004 |
| WO | WO 2004/087006 | 10/2004 |
| WO | WO 2004/091441 | 10/2004 |
| WO | WO 2005/009295 | 2/2005 |
| WO | WO 2005/013853 | 2/2005 |
| WO | WO 2005/023153 | 3/2005 |
| WO | WO 2006/036939 | 4/2006 |
| WO | WO 2006/047520 | 5/2006 |
| WO | WO 2007/035805 | 3/2007 |
| WO | WO 2007/053187 | 5/2007 |
| WO | WO 2007/146411 | 12/2007 |
| WO | WO 2008/005111 | 1/2008 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

"Drug Delivery Stent With Holes Located on Neutral Axis" Research Disclosure, Kenneth Mason Publications, Hampshire, CB, No. 429, Jan. 2000, p. 13, XP00976354.

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," Journal of Controlled Release 92 (2003) pp. 83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., Parallel Production of Oligonucleotide Arrays Using Membranes and Reagent Jet Printing, BioTechniques 25:886-890 (Nov. 1998).

Chu et al., "Preparation of Thermo-Responsive Core-Shell Microcapsules with a Porous Membrane and Poly(N-isopropylacrylamide) Gates," J Membrane Sci, Oct. 15, 2001; 192(1-2):27-39.

Tilley, "Biolimus A9-Eluting Stent Shows Promise," Medscape Medical News, Oct. 5, 2004; retrieved from the internet: <http://www.medscape.com/viewarticle/490621>, 2 pages total.

Weir et al., "Degradation of poly-L-lactide. Part 2: increased temperature accelerated degradation," Proc Inst Mech Eng H. 2004;218(5):321-30.

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

Supplementary European Search Report of EP Patent Application No. 07758831, dated Dec. 14, 2009.

The State Intellectual Property Office of the Republic of China, Application No. 200880100150.2, First Office Action date of dispatch Oct. 26, 2011, 11 pages.

The State Intellectual Property Office of the People's Republic of China, Application No. 200880100150.2, Second Office Action date of dispatch Jul. 25, 2012, 23 pages.

The State Intellectual Property Office of the People's Republic of China, 200880100150.2, Third Office Action date of dispatch Apr. 12, 2013, 26 pages.

International Search Report and Written Opinion of PCT Application No. PCT/US2008/061041, mailed Nov. 7, 2008, 13 pages total.

Office Action of Japanese Patent Application No. 2006-547139, mailed Jun. 15, 2010, 5 pages total. (English translation included).

Supplementary European Search Report of EP Patent Application No. 02804509, dated Dec. 13, 2006, 2 pages total.

Supplementary European Search Report of EP Patent Application No. 04749567, dated Sep. 11, 2006, 2 pages total.

International Search Report and Written Opinion of PCT Application No. PCT/US2007/086864, mailed May 13, 2008, 13 pages total.

\* cited by examiner

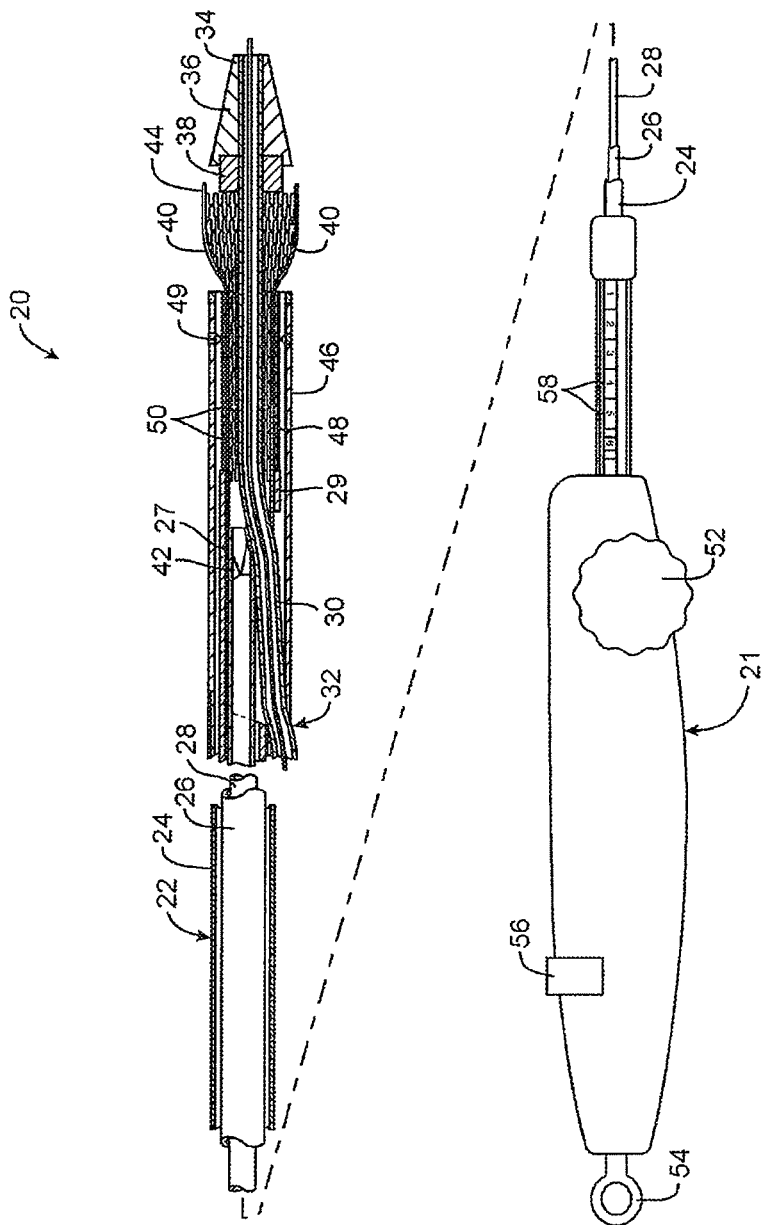

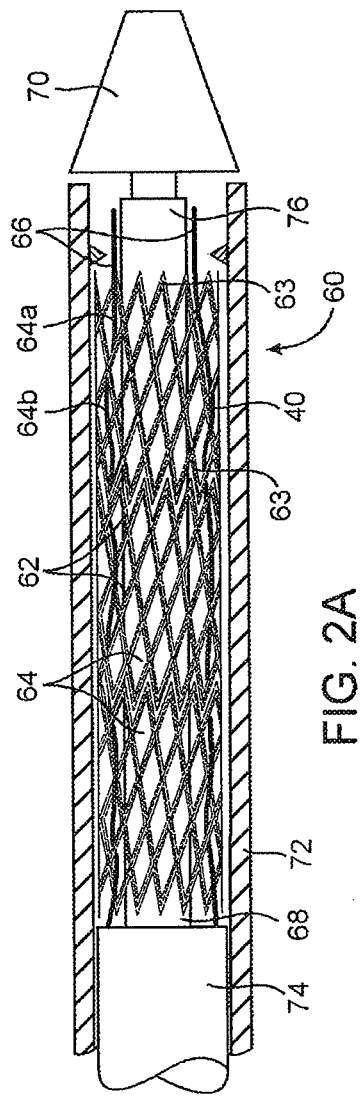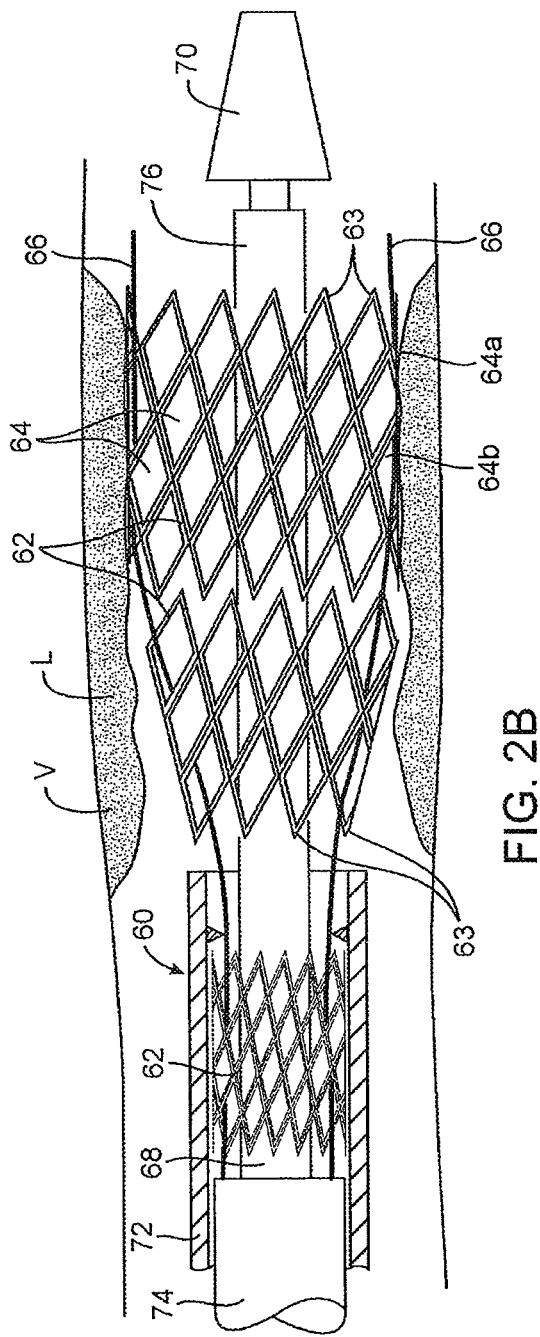

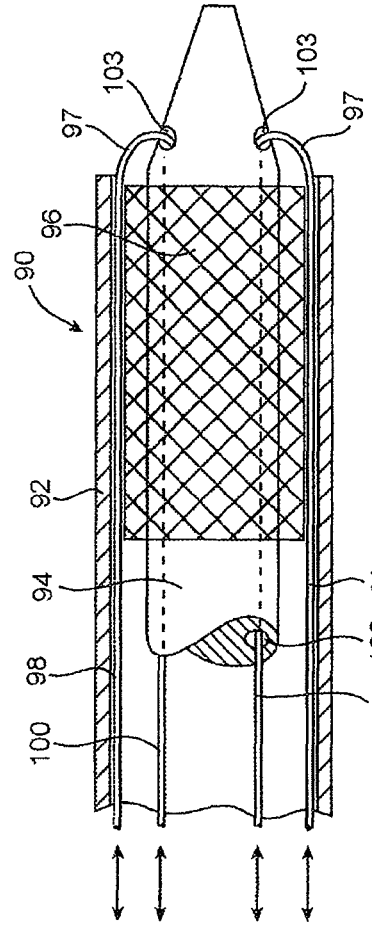
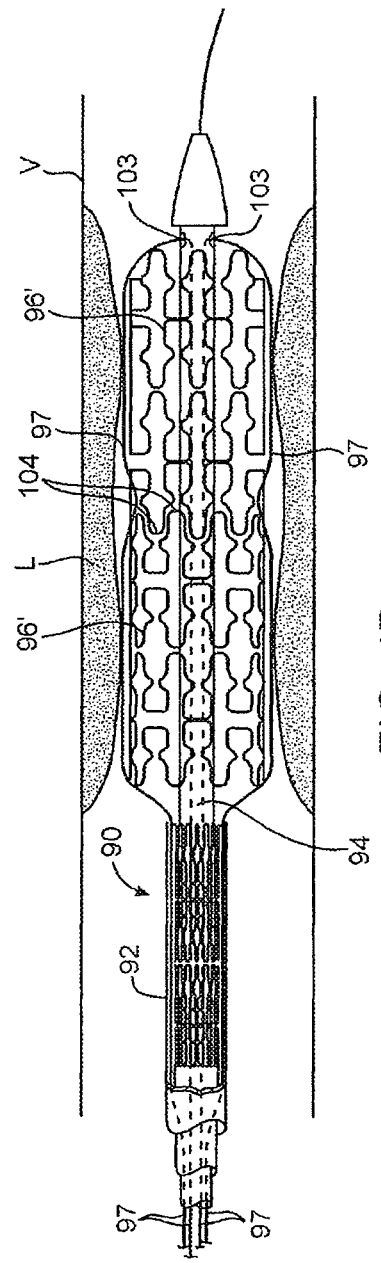

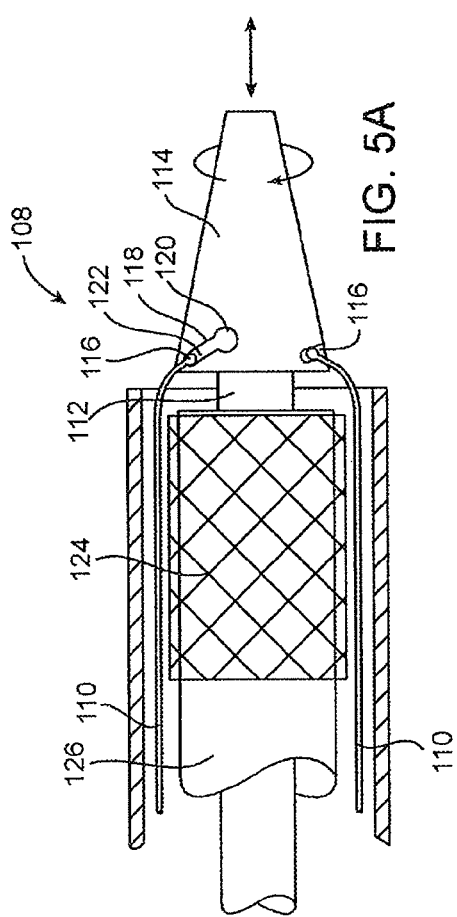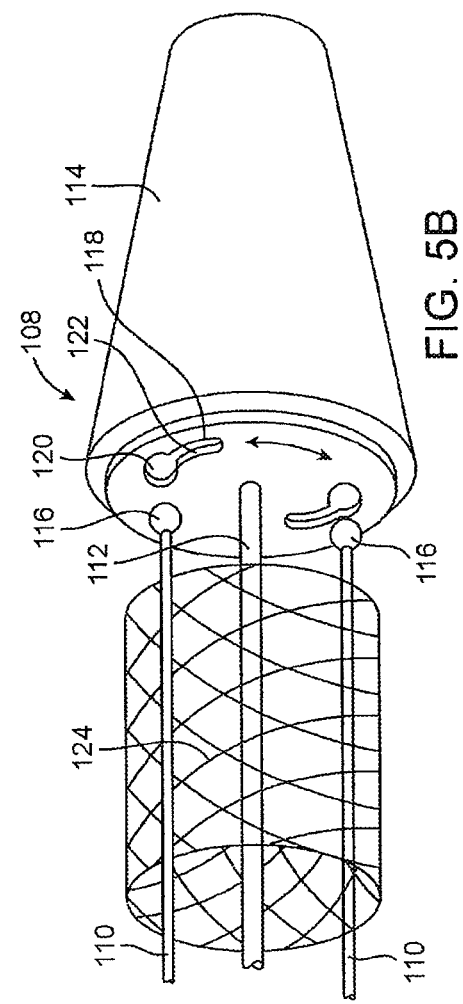

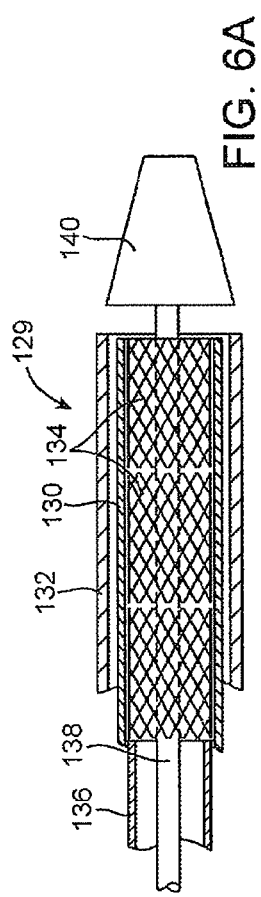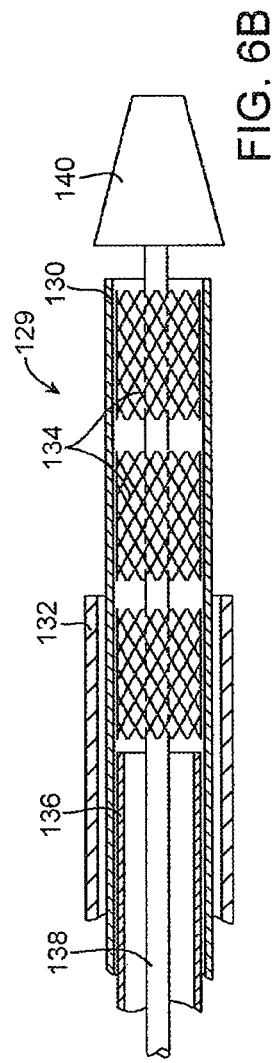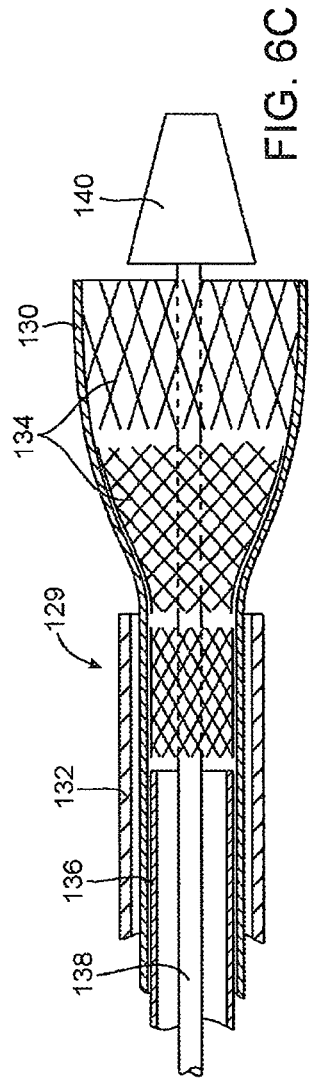

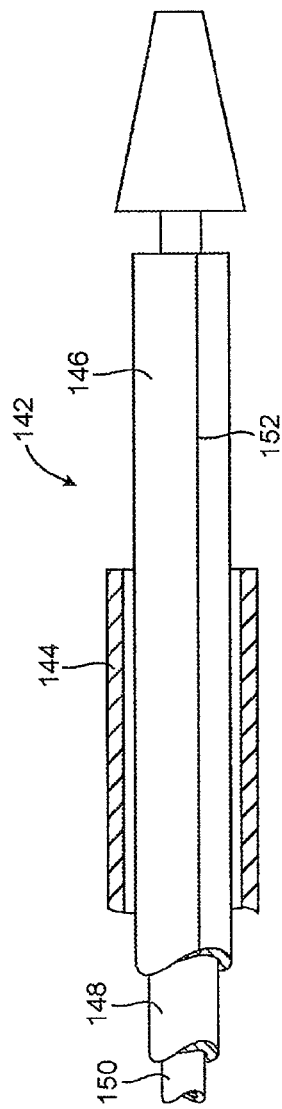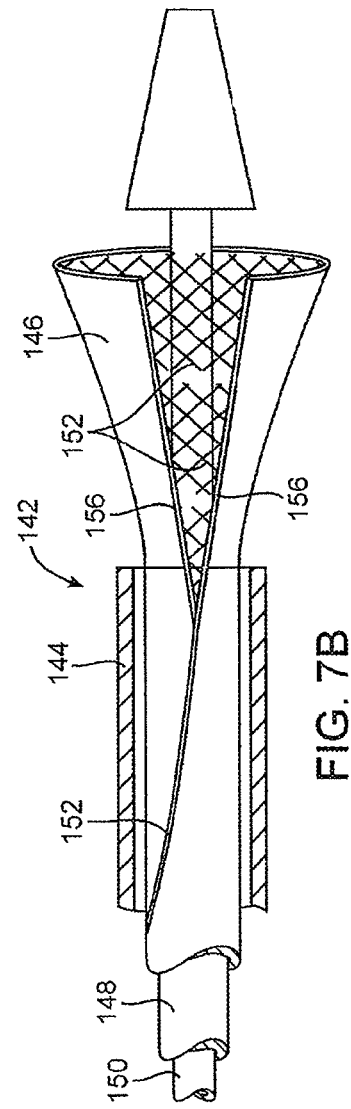

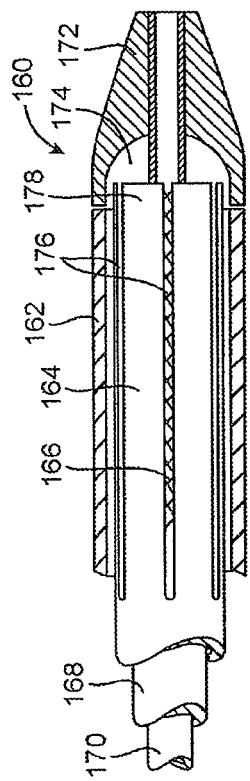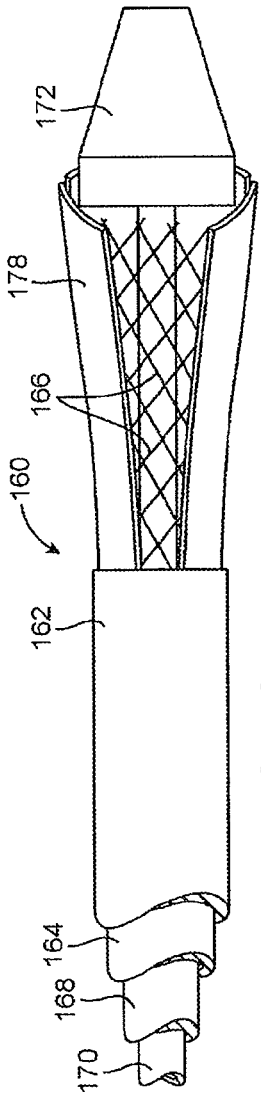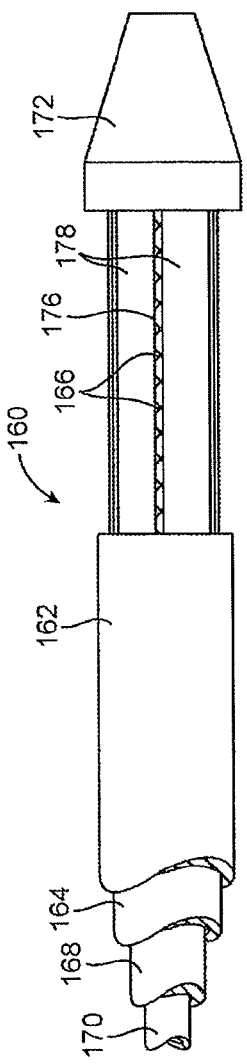

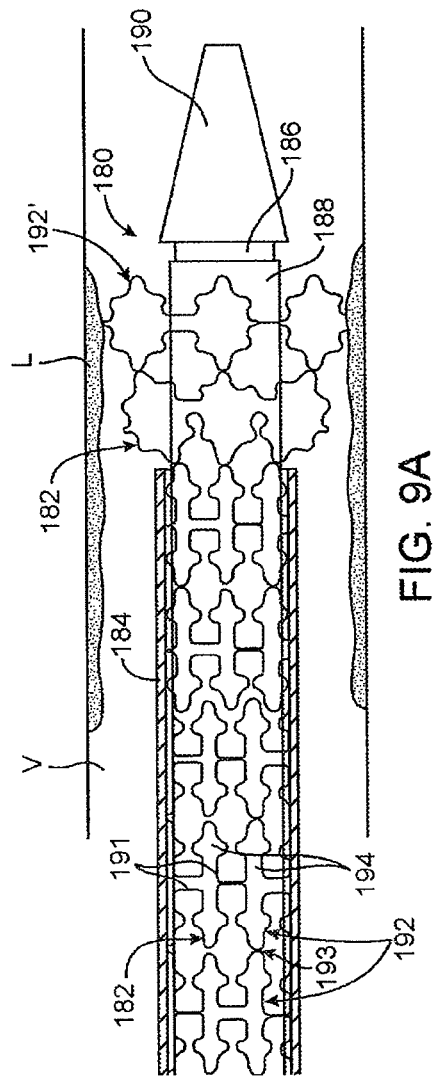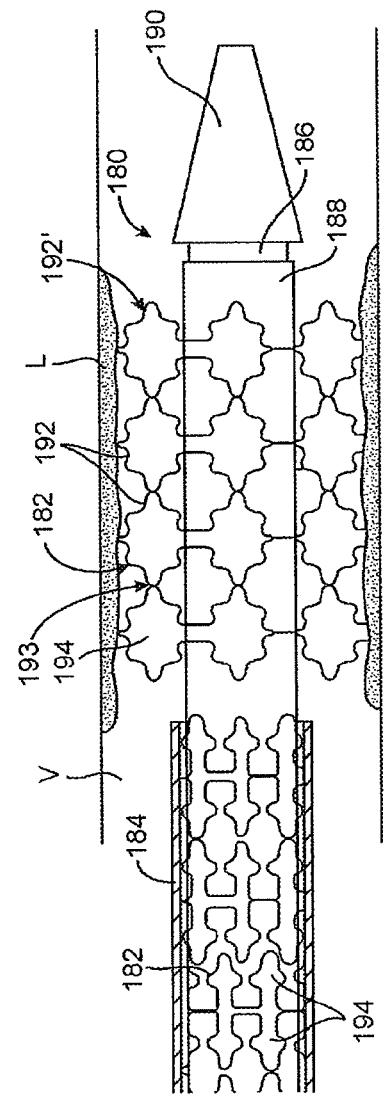
FIG. 9A
FIG. 9B

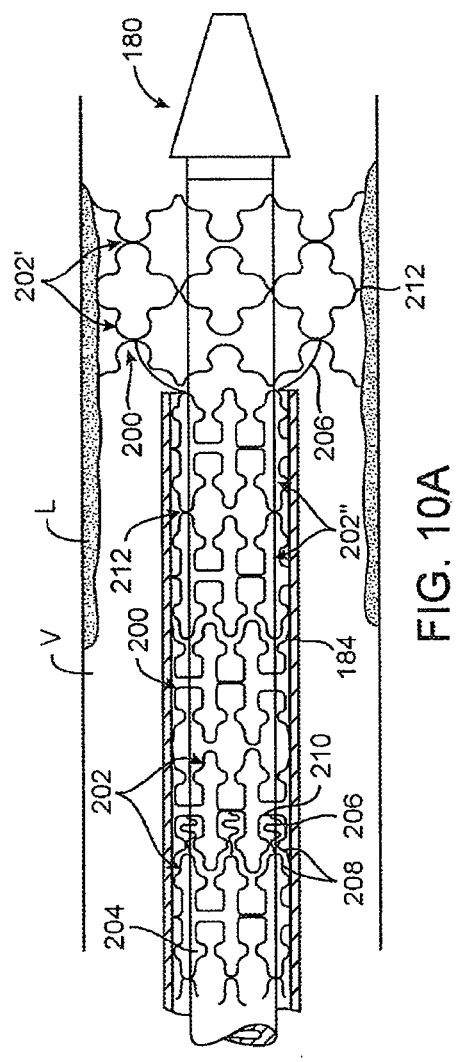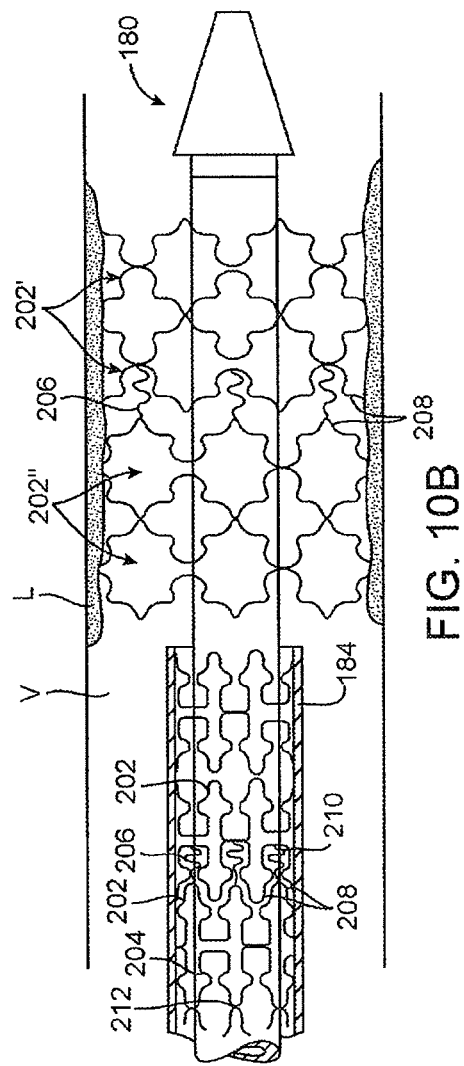

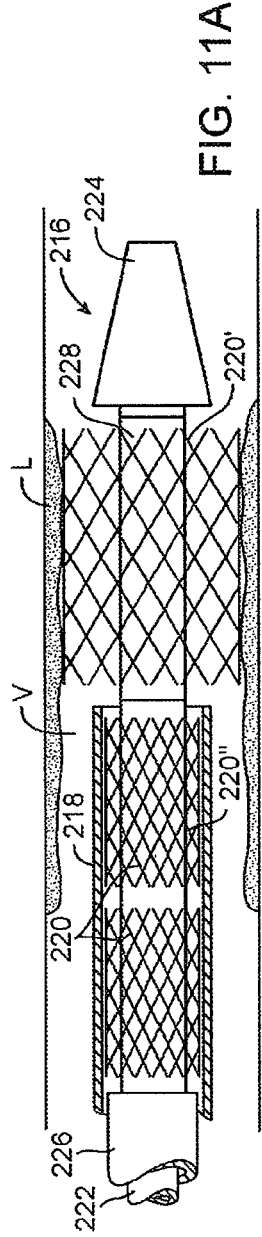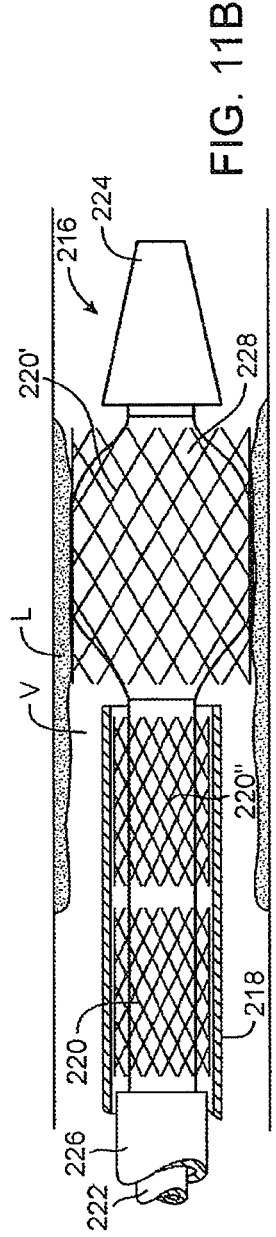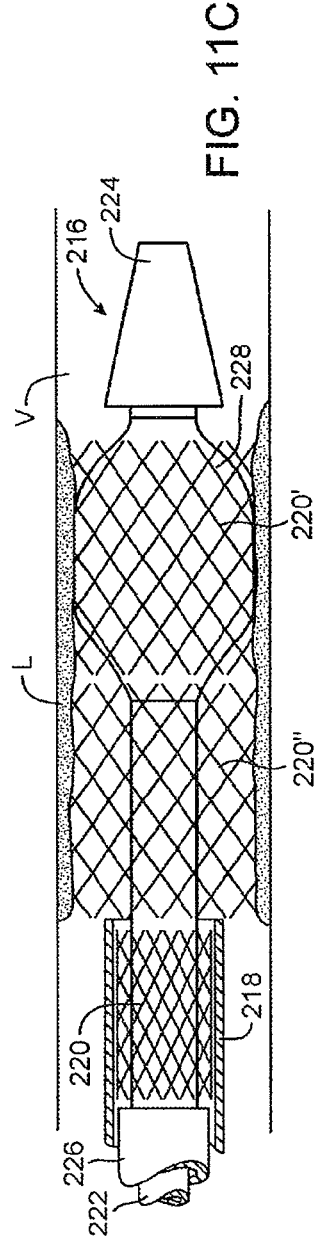

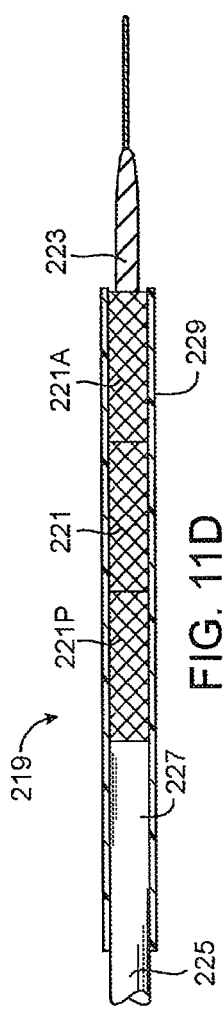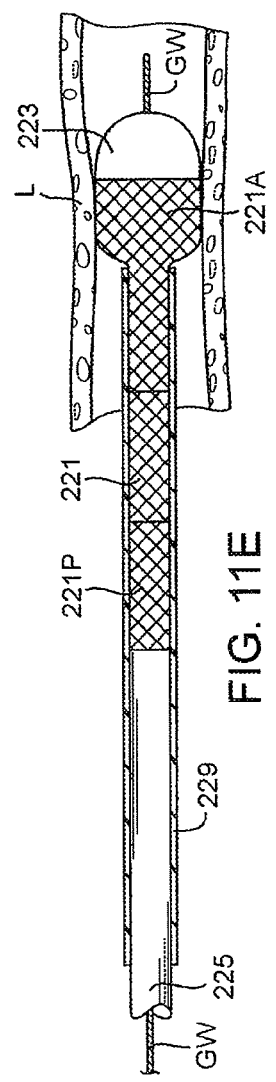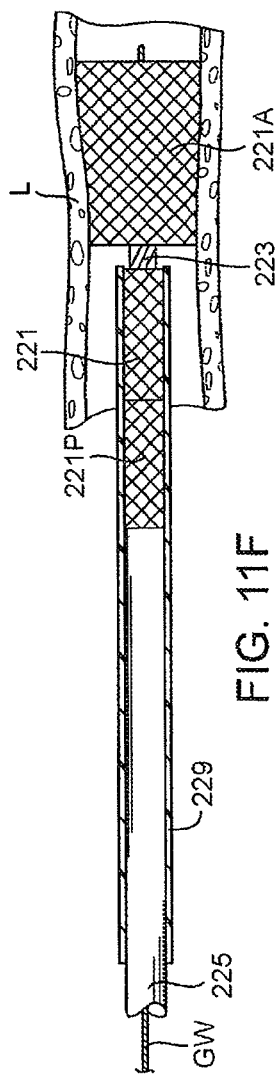

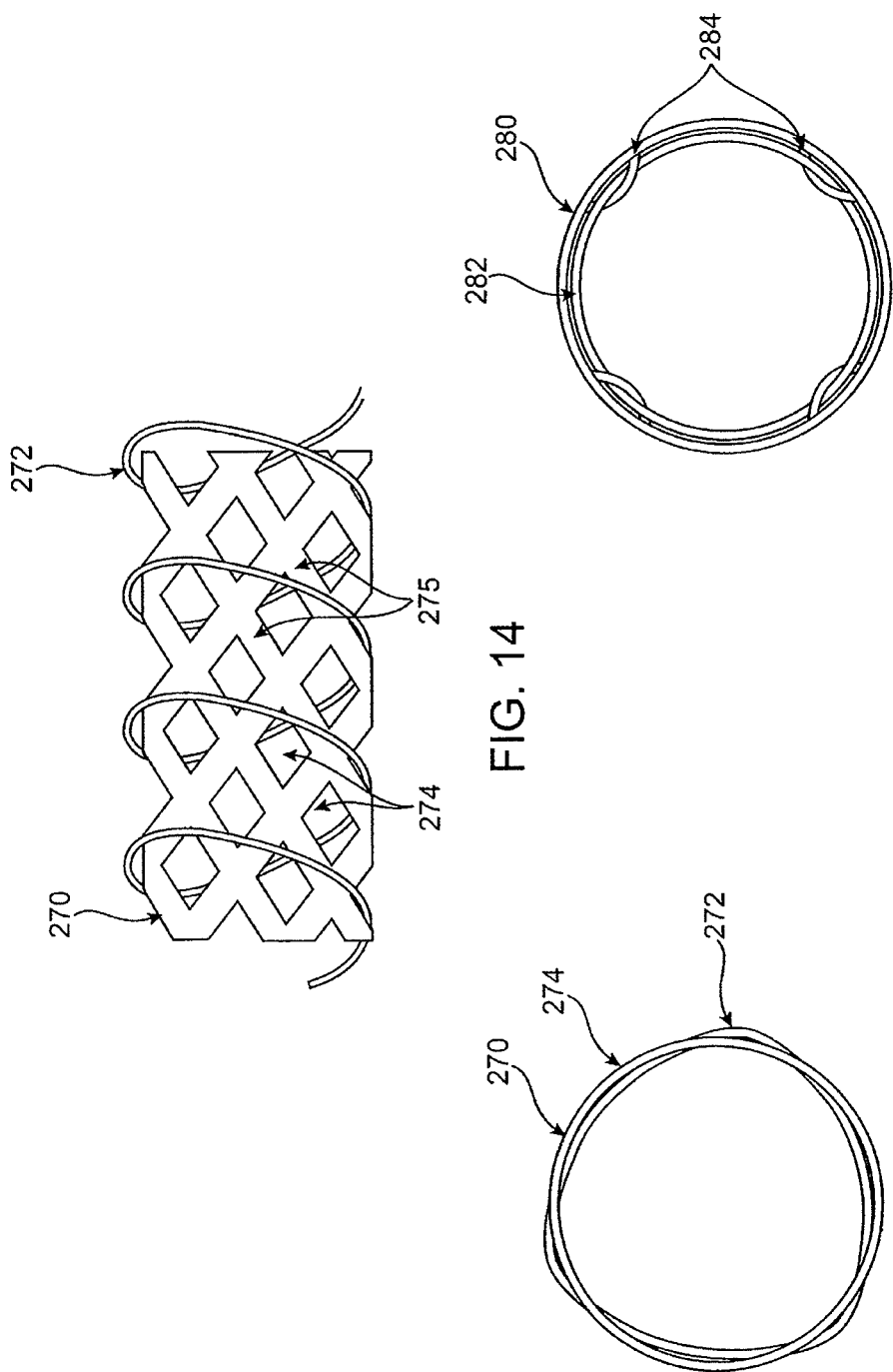

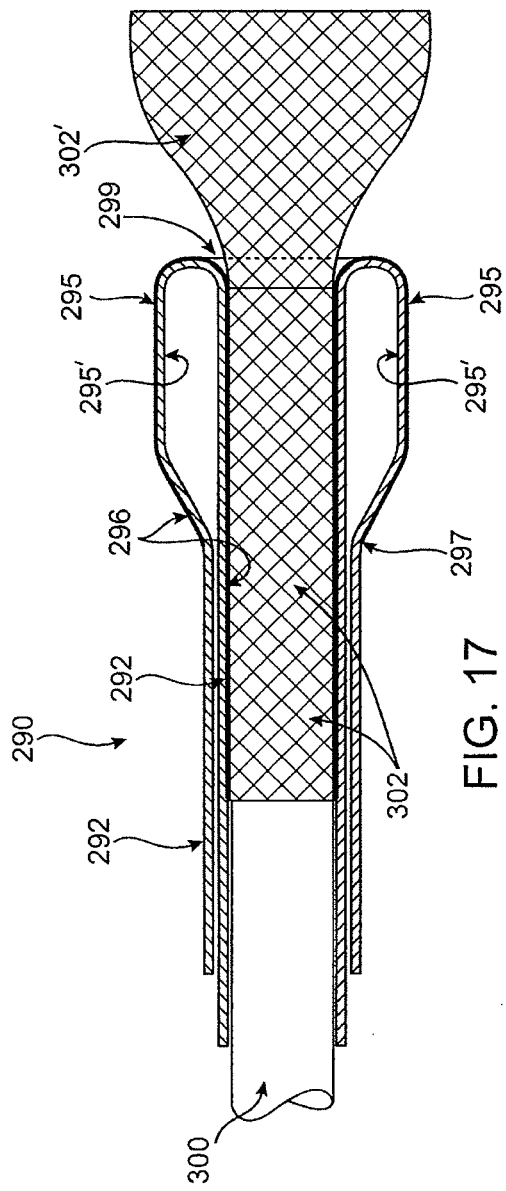
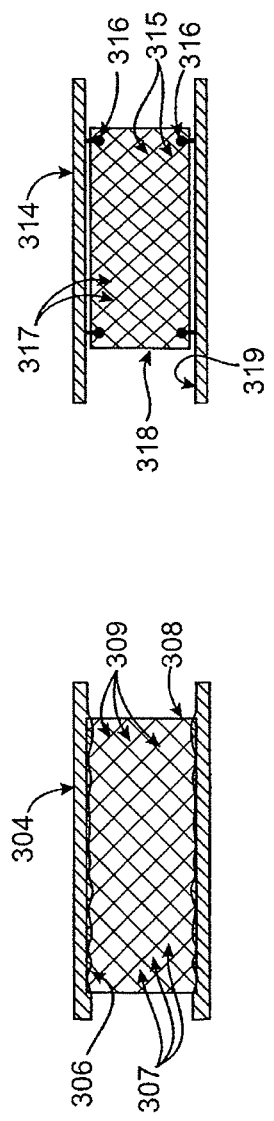
FIG. 17
FIG. 18
FIG. 19

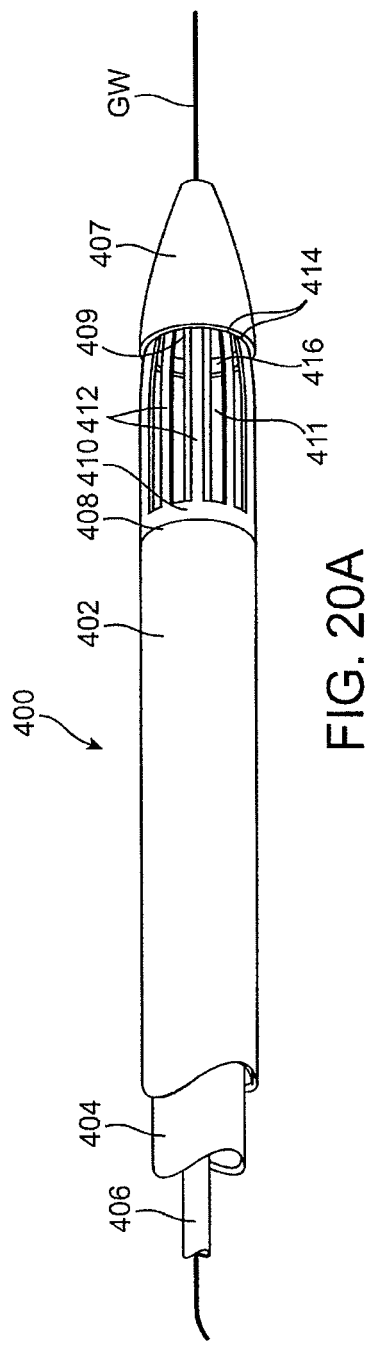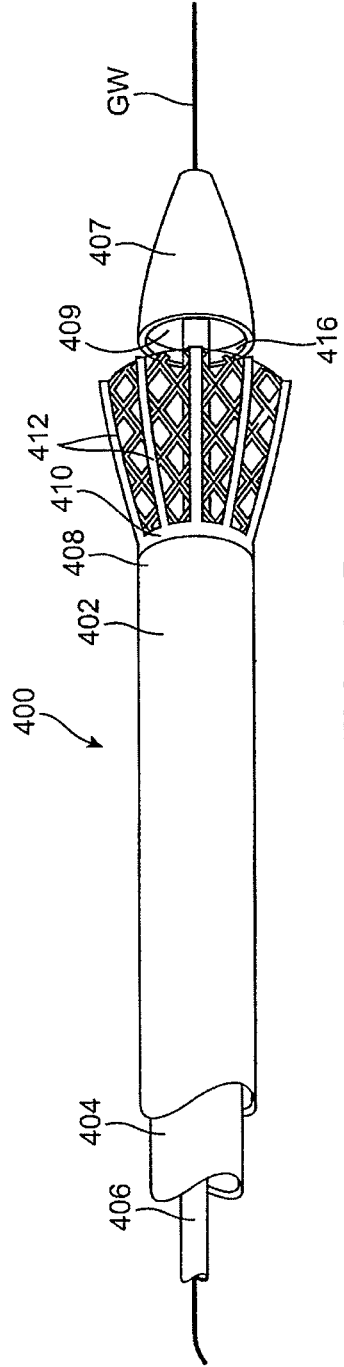

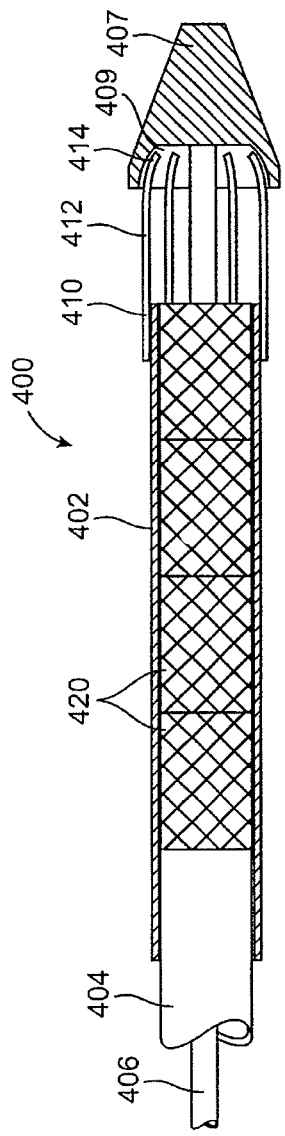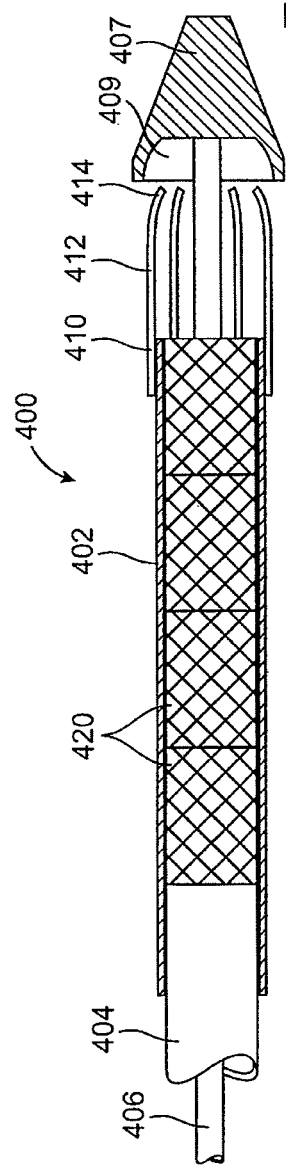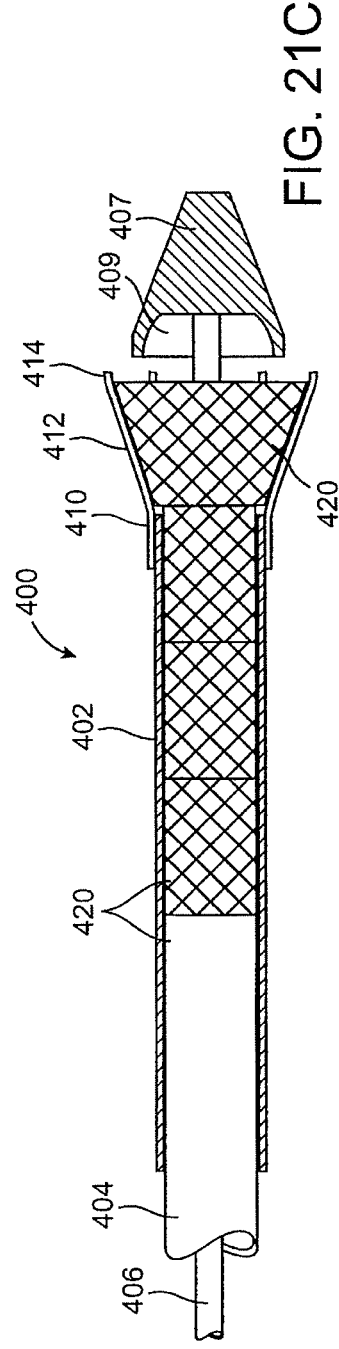

DEVICES AND METHODS FOR CONTROLLING EXPANDABLE PROSTHESES DURING DEPLOYMENT

CROSS REFERENCE TO RELATED APPLICATIONS

The present application is a continuation of U.S. patent application Ser. No. 10/957,079 filed Sep. 30, 2004 which is a continuation-in-part of U.S. patent application Ser. No. 10/879,949, filed Jun. 28, 2004, the full disclosures of which are hereby incorporated by reference.

BACKGROUND OF THE INVENTION

Stents are tubular prostheses designed for implantation in a vessel to maintain patency of the vessel lumen. Stents are used in various vessels throughout the body, including the coronary arteries, femoral arteries, iliac arteries, renal artery, carotid artery, vascular grafts, biliary ducts, trachea, and urethra, to name some examples. Stents are typically implanted by means of long and flexible delivery catheters that carry the stents in a compact, collapsed shape to the treatment site and then deploy the stents into the vessel. In some applications, balloon expandable stents are used. These stents are made of a malleable metal such as stainless steel or cobalt chromium and are expanded by means of a balloon on the tip of the delivery catheter to plastically deform the stent into contact with the vessel wall. In other applications, self-expanding stents are used. These are made of a resilient material that can be collapsed into a compact shape for delivery via catheter and that will self-expand into contact with the vessel when deployed from the catheter. Materials commonly used for self-expanding stents include stainless steel and elastic or superelastic alloys such as nickel titanium (Nitinol™).

While self-expanding stents have demonstrated promise in various applications, such stents face a number of challenges. One such challenge is that in some cases the disease in a vessel may be so extensive that a stent of very long length, e.g. 30-200 mm, is called for. Currently available stents are typically less than 30 mm in length, and suffer from excessive stiffness if made longer. Such stiffness is particularly problematic in peripheral vessels such as the femoral arteries, where limb movement requires a high degree of flexibility in any stent implanted in such vessels.

To overcome the stiffness problem, the idea of deploying multiple shorter stents end-to-end has been proposed. However, this approach has suffered from several drawbacks. First, currently available delivery catheters are capable of delivering only a single stent per catheter. In order to place multiple stents, multiple catheters must be inserted, removed and exchanged, heightening risks, lengthening procedure time, raising costs, and causing excessive material waste. In addition, the deployment of multiple stents end-to-end suffers from the inability to accurately control stent placement and the spacing between stents. This results in overlap of adjacent stents and/or excessive space between stents, which is thought to lead to complications such as restenosis, the renarrowing of a vessel following stent placement. With self-expanding stents the problem is particularly acute because as the stent is released from the catheter, its resiliency tends to cause it to eject or "watermelon seed" distally from the catheter tip by an unpredictable distance. During such deployment, the stent may displace not only axially but rotationally relative to the delivery catheter resulting in inaccurate, uncontrollable, and unpredictable stent placement.

Interleaving stents or stent segments such as those disclosed in co-pending application Ser. No. 10/738,666, filed Dec. 16, 2003, which is incorporated herein by reference, present even greater challenges to conventional delivery systems. Interleaving stents have axially extending elements on each end of the stent that interleave with similar structures on an adjacent stent. Such interleaving minimizes the gap between adjacent stents and increases vessel wall coverage to ensure adequate scaffolding and minimize protrusion of plaque from the vessel wall. However, such interleaving requires that the relative rotational as well as axial positions of the adjacent stents be maintained during deployment to avoid metal overlap and excessive gaps between stents. Conventional delivery systems suffer from the inability to control both the axial and rotational positions of self-expanding stents as they are deployed.

What are needed, therefore, are stents and stent delivery system that overcome the foregoing problems. In particular, the stents and stent delivery systems should facilitate stenting of long vascular regions of various lengths without requiring the use of multiple catheters. Such stents and delivery systems should also provide sufficient flexibility for use in peripheral vessels and other regions where long and highly flexible stents might be required. In addition, the stents and stent delivery systems should enable the delivery of multiple stents of various lengths to one or more treatment sites using a single catheter without requiring catheter exchanges. Further, the stents and stent delivery systems should facilitate accurate and repeatable control of stent placement and inter-stent spacing to enable deployment of multiple self-expanding stents end-to-end in a vessel at generally constant spacing and without overlap. Moreover, the stents and delivery systems should enable the deployment of interleaving stents or stent segments with precision and control over both the axial spacing and rotational position of each stent or segment.

BRIEF SUMMARY OF THE INVENTION

The present invention provides prostheses, prosthesis delivery systems, and methods of prosthesis deployment that enable the precise and controllable delivery of multiple prostheses using a single delivery catheter. The prostheses, delivery systems, and methods of the invention provide for the precise control of prosthesis placement so that inter-prosthesis spacing is maintained at a constant and optimum distance. In some embodiments, both axial and rotational displacement of the prostheses relative to the delivery catheter is controlled during deployment, enabling the delivery of multiple prostheses that interleave with one another without overlap. The prostheses, prosthesis delivery systems, and methods of the invention further enable the length of prostheses to be customized in situ to match the length of the site to be treated. The invention is particularly useful for delivery of self-expanding prostheses, but balloon expandable prostheses are also contemplated within the scope of the invention. The invention is well-suited to delivery of stents to the coronary arteries and to peripheral vessels such as the popliteal, femoral, tibial, iliac, renal, and carotid arteries. The invention is further useful for delivery of prostheses to other vessels including biliary, neurologic, urinary, reproductive, intestinal, pulmonary, and others, as well as for delivery of other types of prostheses to various anatomical regions, wherever precise control of prosthesis deployment is desirable.

In a first aspect of the present invention, a prosthesis delivery catheter includes an outer shaft forming a first lumen, a plurality of self-expanding tubular prostheses carried within the first lumen, and a movable coil member interactive with the prostheses to control expansion of the prostheses when the prostheses are deployed from the first lumen. The prostheses are generally adapted to radially expand upon deployment from the first lumen.

In some embodiments, the coil member is removable from the deployed prostheses by rotating the coil member. In some embodiments, the prostheses have sidewalls with a plurality of openings, the coil member being threaded through the openings. Alternatively, the prostheses may include a plurality of struts, at least one of the struts being bent inwardly, with the coil member being threaded through the inwardly bent struts. Optionally, the coil member may be radially expandable to allow controlled expansion of the prostheses. In some embodiments, a distal portion of the coil member is retractable into the outer shaft following deployment of the selected number of prostheses. In some embodiments, the prostheses are disposed within the coil member.

In various embodiments, the coil member may include a plurality of loops forming a helix. For example, in some embodiments between 2 and 6 loops are disposed in each prosthesis. In other embodiments, more than 6 loops are disposed in each prosthesis. In some embodiments, the coil member comprises a plurality of loops contacting each other to form a continuous tube.

Optionally, the delivery catheter may also include a deployment mechanism for deploying a selected number of prostheses from the inner lumen. In some embodiments, for example, the deployment mechanism includes a pushing element slidably disposed in the first lumen, the pushing element being in engagement with at least one of the prostheses to advance the prostheses distally relative to the outer shaft. Optionally, adjacent ends of adjacent prostheses may be interleaved to resist rotation of the prostheses relative to each other. In one embodiment, a distal end of the pushing element is interleaved with a proximal end of a proximal-most prosthesis to resist rotation of the prostheses. In these or other embodiments, the coil member may optionally be configured to maintain rotational position of the prostheses relative to each other.

In another aspect of the present invention, a prosthesis delivery catheter for delivering prostheses into a vessel lumen includes an outer shaft forming a first lumen, an inner shaft slidably disposed within the first lumen, an evertible tube having a first end coupled with a distal end of the outer shaft and a second end coupled with a distal end of the inner shaft, and a plurality of self-expanding tubular prostheses carried within the evertible tube. Again, the prostheses are generally adapted to radially expand upon deployment from the evertible tube. Moving the outer shaft proximally relative to the inner shaft everts a distal portion of the evertible tube so as to deploy one or more of the prostheses.

In some embodiments, an inner surface of the inner shaft comprises at least one adherent element for releasably holding the prostheses to the inner surface. For example, in one embodiment, the adherent element comprises a tacky surface coating. Alternatively, the adherent element may comprise a softenable material into which the prostheses are removably embedded. In other embodiments, the adherent element comprises a plurality of inwardly-facing protrusions positioned to extend through openings in the prostheses. Such protrusions may have any of a number of shapes in various embodiments, such as but not limited to mushroom-shaped, L-shaped, T-shaped, hook-shaped, rounded, spiked, pyramidal, barbed, arrow-shaped or linear. In yet other embodiments, the adherent element may comprise a structure such as but not limited to bumps, bristles, spines, ridges ribs, waves, grooves, pits, channels, detents or random surface irregularities.

In another aspect of the present invention, a method of delivering one or more prostheses to a treatment site in a vessel involves: positioning a delivery catheter at the treatment site, the delivery catheter carrying a plurality of self-expanding prostheses; selecting a desired number of the prostheses to deploy; deploying the desired number of prostheses from the delivery catheter into the vessel, each prosthesis expanding into contact with the vessel upon deployment; controlling axial displacement of each of the selected number of prostheses relative to the delivery catheter during deployment of the prostheses with an expandable coil member coupled with the prostheses; and removing the expandable coil member from the deployed prostheses.

In some embodiments, removing the coil member involves rotating the coil member. For example, the coil member may be helically threaded through the prostheses such that rotating the coil member unthreads the coil member from one or more prostheses. In some embodiments, the method also involves controlling the rotational displacement of the selected number of prostheses relative to the delivery catheter during deployment of the prostheses. In one embodiment, for example, the rotational displacement is controlled by interleaving adjacent ends of adjacent prostheses and interleaving a proximal end of a proximal-most prosthesis with a portion of the catheter device. In some embodiments, a distal portion of the coil member expands with the selected number of prostheses.

In yet another aspect of the present invention, a method of delivering one or more prostheses to a treatment site in a vessel involves: positioning a delivery catheter at the treatment site, the delivery catheter carrying a plurality of self-expanding prostheses within an evertible tube; selecting a desired number of the prostheses to deploy; and everting a distal portion of the evertible tube to deploy the desired number of prostheses from the delivery catheter into the vessel, each prosthesis expanding into contact with the vessel upon deployment. In some embodiments, the distal portion of the evertible tube is everted by sliding an outer shaft of the catheter device relative to an inner shaft of the catheter device. For example, in some embodiments, a distal end of the outer shaft is coupled with a distal end of the evertible tube such that sliding the outer shaft proximally relative to the inner shaft causes the distal end of the evertible tube to bend outward and fold over on itself.

Optionally, the method may further involve controlling axial displacement of each of the selected number of prostheses relative to the delivery catheter during deployment of the prostheses by contacting an adherent inner surface of the evertible tube with the prostheses. In one embodiment, for example, the adherent surface maintains engagement with the prostheses until the distal portion of the evertible tube is peeled away from the prostheses. In some embodiments, the adherent surface comprises a friction-inducing coating or friction-inducing surface feature. In some embodiments, contacting the adherent surface with the prostheses involves releasably coupling one or more retention structures on the inner surface with the prostheses. Alternatively, contacting the adherent surface with the prostheses may involve embedding the prostheses in a deformable material on the adherent inner surface.

In a further aspect of the invention, a prosthesis delivery catheter comprises an outer shaft having a distal end and a first lumen, a plurality of self-expanding tubular prostheses carried within the first lumen, the prostheses being adapted to radially expand upon deployment from the first lumen, and a control member extending distally from the distal end of the outer shaft and defining an interior communicating with the first lumen for receiving one or more of the prostheses. The control member has an undeflected shape when not engaged by one of the prostheses and is configured to deflect radially outwardly when engaged by a prosthesis during expansion thereof. The control member is also configured to resiliently return to the undeflected shape when the prosthesis is removed from the interior. In one embodiment, the control member generally includes a plurality of deflectable tines having free distal ends received within an aperture on the nose cone or nose piece of the catheter. Optionally, the control member may further include a plurality of webs between the tines. In an alternative embodiment, the control member may comprise a distensible tubular structure.

Further aspects of the nature and advantages of the invention will be apparent from the following detailed description of various embodiments of the invention taken in conjunction with the drawings.

BRIEF DESCRIPTION OF THE DRAWINGS

FIG. 1 is a side cut-away view of a prosthesis delivery catheter according to the invention.

FIG. 2A is a side cross-sectional view of a distal portion of a prosthesis delivery catheter according to the invention in a further embodiment thereof.

FIG. 2B is a side cross-sectional view of the prosthesis delivery catheter of FIG. 2A showing the deployment of prostheses in a vessel.

FIG. 4A is a side cross-section of a distal portion of a prosthesis delivery catheter according to the invention in a further embodiment thereof.

FIG. 4B is a side cross-section of the prosthesis delivery catheter of FIG. 4A showing the deployment of prostheses in a vessel.

FIG. 5A is a side cross-section of a distal portion of a prosthesis delivery catheter according to the invention in a further embodiment thereof.

FIG. 5B is an oblique view of a distal portion of a prosthesis delivery catheter according to the invention in yet another embodiment thereof.

FIGS. 6A-6C are side cross-sectional views of a distal portion of a prosthesis delivery catheter according to the invention in still another embodiment thereof, showing the outer shaft unretracted, outer shaft retracted with sleeve unexpanded, and sleeve with stents expanded, respectively.

FIGS. 7A-7B are side cross-sectional views of a distal portion of a prosthesis delivery catheter according to the invention in another embodiment thereof, showing outer shaft retracted with sleeve unexpanded, and outer shaft retracted with sleeve and stents expanded, respectively.

FIGS. 8A-8C are side cross-sectional views of a distal portion of a prosthesis delivery catheter according to the invention in a further embodiment thereof, showing the outer shaft unretracted, outer shaft retracted with sleeve unexpanded, and sleeve with stents expanded, respectively.

FIGS. 9A-9B are side cross-sectional views of a distal portion of a prosthesis delivery catheter in a vessel according to the invention in another embodiment thereof, showing outer shaft retracted with prosthesis partially deployed, and prosthesis fully deployed, respectively.

FIGS. 10A-10B are side cross-sectional views of a distal portion of a prosthesis delivery catheter in a vessel according to the invention in yet another embodiment thereof, showing outer shaft retracted with prosthesis partially deployed, and prosthesis fully deployed, respectively.

FIGS. 11A-11C are side cross-sectional views of a distal portion of a prosthesis delivery catheter in a vessel according to the invention in yet another embodiment thereof, showing a first prosthesis deployed, an expandable member expanded within the first prosthesis, and a second stent deployed with expandable member expanded in the first prosthesis, respectively.

FIGS. 11D-11F are side cross-sectional views of a distal portion of a prosthesis delivery catheter according to another embodiment of the invention, showing the delivery catheter prior to stent deployment, the deployment of a first prosthesis in a vessel, and a deployed prosthesis in the vessel, respectively.

FIG. 14 is a side view of a prosthesis coupled with a coil member according to one embodiment of the invention.

FIG. 15 is an end-on view of a prosthesis coupled with a coil member according to one embodiment of the invention.

FIG. 16 is an end-on view of a prosthesis coupled with a coil member according to another embodiment of the invention.

FIG. 17 is a cross-sectional side view of a distal end of a prosthesis delivery catheter having an evertible tube according to one embodiment of the present invention.

FIG. 18 is a cross-sectional side view of a portion of an evertible tube of a prosthesis delivery catheter according to one embodiment of the present invention.

FIG. 19 is a cross-sectional side view of a portion of an evertible tube of a prosthesis delivery catheter according to another embodiment of the present invention.

FIGS. 20A-20B are oblique views a prosthesis delivery catheter according to the invention in a further embodiment thereof, before and during deployment of a prosthesis, respectively.

FIGS. 21A-21E are side cross-sectional views of the prosthesis delivery catheter of FIGS. 20A-B, illustrating the steps of deploying a prosthesis according to the invention.

DETAILED DESCRIPTION OF THE INVENTION

Figure 3B:
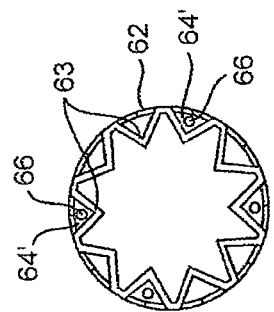
FIGS. 3A-3C are perspective, side, and end views respectively of a prosthesis coupled to control wires according to further embodiments of the invention.

Referring to FIG. 1, a first embodiment of a prosthesis delivery catheter according to the invention is illustrated. Delivery catheter 20 may have any of various constructions, including that described in co-pending application Ser. No. 10/637,713, filed Aug. 8, 2003, which is incorporated herein by reference. Delivery catheter 20 has a handle assembly 21 and an elongated catheter body 22 that includes three concentric tubular shafts all axially slidable relative to one another: an outer shaft 24, a pusher 26, and an inner shaft 28. Pusher 26 has a distal extension 27 to which a pusher ring 29 is fixed. In a distal region of the catheter body 22, a guidewire tube 30 extends slidably through a port 32 in outer shaft 24 and through pusher ring 29 and has a distal end 34, to which is mounted a nosecone 36 and a stop member 38.

Delivery catheter 20 further includes one or more stent expansion control members, which in the illustrated embodiment comprise a plurality of control wires 40. Preferably, one or more pairs of control wires 40 are mounted on opposing sides of delivery catheter 20, e.g. four control wires 40 offset 90° from each other. Control wires 40 are fixed at their proximal ends 42 to inner shaft 28, and have free distal ends 44.

Outer shaft 24 has a distal extremity 46 defining a first lumen 48. A plurality of stents 50 are disposed in a collapsed configuration within first lumen 48. Stents 50 are preferably composed of a resilient material such as stainless steel or Nitinol so as to self-expand from the collapsed configuration to a radially expanded configuration when deployed from first lumen 48. While stents 50 as illustrated have a wave-like or undulating pattern in a plurality of interconnected circumferential members, the pattern illustrated is merely exemplary and the stents of the invention may have any of a variety of strut shapes, patterns, and geometries. From 2 up to 10 or more stents may be carried by outer shaft 24. Optionally, a valve member 49 is mounted within first lumen 48 to facilitate separating those stents 50 to be deployed from those to remain within outer shaft 24, as described in co-pending application Ser. No. 10/412,714, filed Apr. 10, 2003, which is incorporated herein by reference.

Control wires 40 run along the outside of stents 50 or through the interior of stents 50, are threaded through openings in the walls of stents 50 or are otherwise coupled with stents 50 to control the deployment thereof, as described more fully below. Control wires 40 are composed of a resilient material such as stainless steel, Nitinol, or a suitable polymer, and are preferably generally straight and biased inwardly against guidewire tube 32 or to a position generally parallel to the axial direction. In FIG. 1, outer shaft 24 has been retracted to expose a plurality of stents 50 which are partially expanded and remain coupled to or restrained by control wires 40, as explained in greater detail below.

Handle assembly 21 has a rotatable retraction knob 52 coupled to a shaft housing 53, to which outer shaft 24 is fixed. By rotating retraction knob 52, outer shaft 24 may be retracted proximally relative to pusher 26 and inner shaft 28. A pull ring 54 is coupled to inner shaft 28, allowing inner shaft 28, and hence control wires 40, to be retracted proximally relative to outer shaft 24. A switch 56 engages and disengages pusher 26 with outer shaft 28, so that pusher 26 either moves with outer shaft 24 or remains stationary as outer shaft 24 is retracted. Indicia 58 on shaft housing 53 indicate the extent of retraction of outer shaft 28 by distance, number of stents, or other suitable measure. Other aspects of handle assembly 21 are described in co-pending application Ser. No. 10/746,466, filed Dec. 23, 2003, which is incorporated herein by reference. Except as stated otherwise, any of the embodiments of the stent delivery catheter described below may incorporate the features and be otherwise constructed as just described.

FIGS. 2A-2B illustrate a distal extremity of a stent delivery catheter 60 according to the invention in a further embodiment thereof. In this embodiment, stents 62 have a series of diamond shaped openings 64 in the walls thereof through which a plurality of control wires 66 are threaded. Stents 62 have a plurality of axially-extending V-shaped points 63 on their distal and proximal ends. These points 63 are configured to interleave or nest with the points 63 on the adjacent stent 62, preferably both in the collapsed and expanded configurations. Various suitable interleaving stent geometries are described in co-pending application Ser. No. 10/736,666, filed Dec. 16, 2003, which is incorporated herein by reference. In order to maintain this interleaving, it is important to maintain the relative rotational and axial positions of the adjacent stents 62 both before and during deployment. By extending through the openings 64 in each stent, control wires 66 keep adjacent stents 62 in rotational alignment as they are advanced forward through the catheter and during deployment. Preferably, each control wire 66 is threaded through at least two openings 64 in each stent 62, one opening 64a near the distal end of each stent 62 and one opening 64b near the proximal end of each stent 62. Alternatively, control wires 66 may be threaded through only a single opening 64 or through three or more openings 64 on each stent 62. Preferably, however, control wires 66 are threaded so that the distal and proximal ends of stents 64 will expand at a generally uniform rate when released, as described below.

Control wires 66 are constructed of a resilient and flexible metal or polymer with sufficient stiffness to provide controlled resistance to the expansion of stents 62. This stiffness may be selected to allow the desired expansion behavior of stents 62 such that "watermelon seeding" is avoided, inter-stent spacing is maintained, and sufficient stent expansion occurs. Control wires 66 may have various cross-sectional geometries, and may be a flat ribbons or blades, round or oval wires, I-beams, or other suitable structures to control stent expansion, maintain spacing and rotational position, and facilitate withdrawal from stents 62 without interference. Control wires 66 may be composed of or coated with a lubricious material such as PTFE to reduce friction during removal from stents 62. In other embodiments, control wires 66 may have surface features, be wrapped with wire windings, or be coated with "sticky" material to increase friction with stents 62. Coatings or surface structures such as scales with one-way frictional effects may also be applied to control wires 66.

As a further alternative, control wires 66 may comprise flexible hollow tubes which are pneumatically or hydraulically controllable to vary their rigidity or stiffness. For example, control wires 66 may comprise polymeric tubes that radially contract or flatten and are very flexible when evacuated of fluid, but which become more rigid when filled with pressurized fluid, such as saline, air, or other liquid or gas. In such an embodiment, control wires 66 are fluidly connected to a pump, syringe, or other suitable fluid delivery mechanism at the proximal end of the delivery catheter. In this way, control wires 66 may be pressurized to increase stiffness as stents 62 are deployed, then evacuated of fluid to reduce their profile and stiffness during withdrawal from the deployed stents.

Stents 62 are slidably positioned over an inner shaft 68, to which is attached a nosecone 70 at the distal end of the device. An outer shaft 72 is slidably disposed over inner shaft 68 and surrounds stents 62, maintaining them in a collapsed configuration, as shown in FIG. 2A. A pusher shaft 74 is slidably disposed over inner shaft 68 and is configured to engage the proximal end of the proximal-most stent 62. Outer shaft 72 is retractable relative to inner shaft 68 in order to expose a desired number of stents 62 as shown in FIG. 2B. When outer shaft 72 is retracted, the exposed stents 62 self-expand to a larger-diameter expanded shape in engagement with lesion L in vessel V. Preferably, at least the distal end of the distal-most stent 62, and more preferably a substantial portion of all stents 62 being deployed, is allowed to expand into engagement with lesion L while control wires 66 remain threaded through openings 64. Control wires 66 are then withdrawn from openings 62, preferably by holding catheter 60 in position and pulling control wires 66 proximally using a suitable mechanism such as that described above with reference to FIG. 1.

Alternatively, the entire catheter 60 may be retracted proximally relative to stents 62 to withdraw control wires 66 from openings 62. Because at least a portion of stents 62 is in engagement with lesion L, stents 62 are held in position in the vessel as control wires 66 are withdrawn.

Optionally, inner shaft 68 may have a balloon 76 mounted thereto near its distal end to enable pre- or post-dilatation of lesion L. In this embodiment, inner shaft 68 has an inflation lumen through which inflation fluid may be delivered to balloon 76. Balloon 76 is preferably as long as the longest lesion that might be treated using catheter 60. To dilate lesion L prior to stent deployment, or to further expand stents 62 after deployment, outer shaft 72 and those of stents 62 remaining therein are retracted relative to inner shaft 68 to expose a desired length of balloon 76. The exposed portion of balloon 76 may then be inflated within the lesion L and/or the deployed stents 62.

Following deployment and any post-dilatation, inner shaft 68 is retracted into outer shaft 72 while maintaining pressure against pusher shaft 74. This slides stents 62 distally along control wires 66 and repositions stents 62 to the distal end of inner shaft 68 so as to be ready for deployment. Catheter 60 may then be repositioned to another vascular location for deployment of additional stents 62.

Figure 3A:
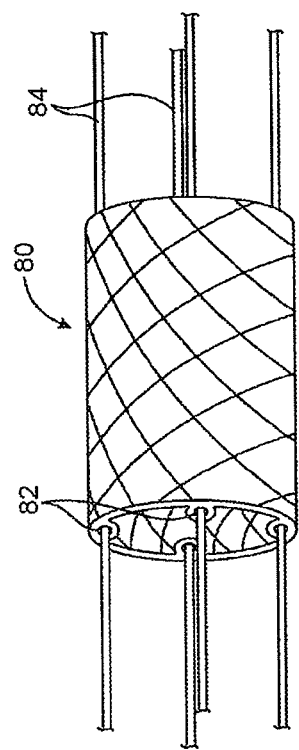

Control wires 66 may be coupled to stents 62 in various ways, some of which depend upon the configuration of stents 62. For example, as shown in FIGS. 3A-B, the points 63 at the ends of each stent 62 may be bent inwardly such that a portion of the openings 64' are oriented axially. Control wires 66 may then be threaded through these axially-oriented openings 64'. Preferably, upon deployment, points 63 are adapted to deform with stent expansion so as to be more parallel to the axial direction, thereby providing a smooth and open flow path through the stent.

Figure 3C:
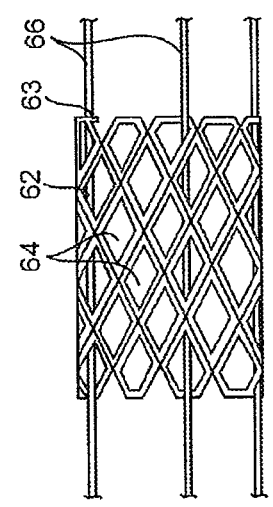

In another embodiment, shown in FIG. 3C, stents 80 have axially-aligned eyelets 82 through which control wires 84 are threaded. These eyelets 82 may be in the interior of stents 82 as shown in FIG. 3C, or such eyelets may be on the exterior surface of stents 82, or could be drilled through one or more of the struts of stents 82. Various other structures may also be used for coupling the stents of the invention to control wires, including hooks, channels, holes, sleeves, and others, disposed on the interior, exterior or end surfaces of the stent, or through the struts themselves. Such structures may by integral with stent struts and of the same material, may be attached to the stent struts and be of same or different material, or may be a biodegradable material that erodes and eventually is absorbed into the body following deployment.

Referring now to FIGS. 4A-4B, in a further embodiment, a stent delivery catheter 90 has an outer shaft 92 slidably disposed over an inner shaft 94, and at least one stent 96 (shown schematically in FIG. 4A) in a collapsed shape within outer shaft 92. A plurality of control wires 97 have an outer extremity 98 outside of inner shaft 94 and an inner extremity 100 extending through one or more lumens 102 and distal ports 103 in inner shaft 94. Both outer portion 98 and inner portion 100 extend proximally to the proximal end of delivery catheter 90. Outer extremities 98 are threaded through openings in the wall of stent 96 or are otherwise coupled thereto as described above so as to resist expansion of stent 96 upon deployment. Control wires 97 thus form a continuous loop from the proximal end of stent delivery catheter 90, through stent 96 and back to the proximal end of the catheter.

FIG. 4B illustrates this embodiment of delivery catheter 90 positioned in a vessel V and carrying plurality of stents 96'. Stents 96' have axial projections 104 at their distal and proximal ends configured to interleave when stents 96' are collapsed within outer shaft 92 and when deployed in vessel V. When outer shaft 92 is retracted to expose one or more stents 96', the expansion of stents 96' can be resisted and controlled by maintaining tension on control wires 97. Tension may be controllably relaxed to allow stents 96' to expand into contact with lesion L, as shown in FIG. 4B. By controlling the expansion in this way, the axial spacing and rotational positions of adjacent stents 96' may be maintained so that gaps and overlaps are minimized and the interleaving of axial projections 104 is maintained. When stents 96' are fully expanded, one end of each control wire 97 may be released at the proximal end of delivery catheter 90 while the other end is pulled to retract the control wires from stents 96'.

In a further embodiment, illustrated schematically in FIGS. 5A-B, delivery catheter 108 is constructed as described above except that control wires 110 are releasably coupled to the distal end of an inner shaft 112 or to nose cone 114. In an exemplary embodiment, control wires 110 have balls 116 at their distal ends configured to be received within slots 118 on the outer surface of nosecone 114 (FIG. 5A) or on the proximal face of nosecone 114 (FIG. 5B; outer shaft not shown for clarity). Slots 118 have an enlarged portion 120 of sufficient size to receive ball 116 and a narrow portion 122 through which balls 116 may not pass. Inner shaft 112 is axially rotatable relative to control wires 110. As in the embodiment of FIGS. 4A-B, with balls 116 held within slots 118, tension may be maintained on control wires 110 to resist expansion of stent 124. Stent 124 may be allowed to expand by gradually relaxing tension on control wires 110. Once stent 124 is fully expanded tension on control wires 110 may be fully relaxed and nosecone 114 then rotated by rotating inner shaft 112, thereby allowing balls 116 to pass through enlarged portions 120. Control wires 110 may then be withdrawn from the deployed stent 124. Nosecone 114 is then retracted or control wires 110 advanced so as to reinsert balls 116 into slots 118. Nosecone 114 is then rotated to align balls 116 with narrow portions 122, again securing the control wires to nosecone 114. Delivery catheter 108 may then be repositioned to deploy additional stents.

Optionally, delivery catheter 108 may include a middle shaft or balloon 126 over which stents 124 are positioned, as shown in FIG. 5A. In this case, inner shaft 112 is slidably and rotatably disposed in an inner lumen though middle shaft or balloon 126. If a balloon is included, it may be used for pre-dilatation of lesions prior to stent deployment, or for further expansion of stent 124 following deployment.

In the foregoing embodiment, control wires 110 will be constructed to have sufficient stiffness to resist rotation, twisting or bending as nosecone 114 is rotated to release control wires 110. Maintaining some tension on control wires 110 as nosecone 114 is rotated may facilitate the release process. In addition, control wires 110 will have sufficient column strength to facilitate reinsertion into slots 118 following deployment of stents 124. Thus the size, material and geometry of control wires 110 will be selected to enable these actions while providing the desired level of control of stent expansion.

In a further embodiment of a stent delivery catheter according to the invention, an expandable sleeve 130 is slidably positioned within outer shaft 132 and carries stents 134 as shown in FIGS. 6A-C. A pusher shaft 136 is slidable within sleeve 130 and engages the proximal-most stent 134. An inner shaft 138 extends through pusher shaft 136 and has a nosecone 140 fixed to its distal end. Sleeve 130, or at least a distal extremity thereof, may be a tube constructed of a resilient deformable material such as urethane or other medical grade elastomer, or may be a tubular mesh, cage, grating, or other suitable structure of flexible and resilient polymer or metal such as stainless steel or Nitinol. The elasticity and stiffness of sleeve 130 are selected to allow stents 134 to expand at the desired rate when deployed from outer shaft 132 without excessive axial or rotational displacement relative to each other or to outer shaft 132. Sleeve 130 is resiliently biased toward an unexpanded shape so that following stent deployment, sleeve 130 returns to a generally tubular shape. Outer shaft 132 is constructed of a material with sufficient radial strength and stiffness to resist expansion of stents 134 and sleeve 130, and may include a metallic or polymeric braid, ribs, rings or other structural reinforcement near its distal end for such purpose.

The interior surface of sleeve 130 optionally may have surface features such as bumps, scales, bristles, ribs, or roughness to enhance friction with stents 134. These features may be configured to have a grain such that they provide more friction against movement in the distal direction than in the proximal direction, or vice versa. Further, such features may be adapted to provide more friction when sleeve 130 is in an unexpanded shape than when it is expanded by stents 134. For example, bristles may be provided that point more in the proximal direction when sleeve 130 is in its unexpanded cylindrical shape, but which point more distally or radially (perpendicular to the surface of sleeve 130) when sleeve 130 is expanded. This allows sleeve 130 to be more easily withdrawn from stents 134 when stents 134 are deployed.

In order to deploy stents 134, delivery catheter 129 is positioned across a vascular lesion so that nosecone 140 is disposed just distally of the distal end of the lesion. Outer shaft 132 is then retracted to expose the desired number of stents 134 (and the associated length of sleeve 130) which will cover the length of the lesion, as shown in FIG. 6B. As outer shaft 132 is retracted, stents 134 are allowed to expand into contact with the lesion as shown in FIG. 6C. Sleeve 130 controls the rate of expansion and maintains the positions of stents 134 so they are deployed precisely at the intended location. Once stents 134 are fully expanded, sleeve 130 may be retracted from between the stents and the lesion until sleeve 130 is again disposed in outer shaft 132. Pressure is maintained on pusher shaft 136 during this process so that the stents 134 remaining in delivery catheter 129 are advanced to the distal end of sleeve 130 and outer shaft 132. Delivery catheter 129 may then be repositioned for deployment of additional stents at other locations.

Referring now to FIGS. 7A-B, in a further embodiment, a delivery catheter 142 may be constructed largely as described in connection with FIGS. 6A-C, including an outer shaft 144, an expandable sleeve 146 slidably disposed therein, a pusher shaft 148, and inner shaft 150. A plurality of stents 152 are carried in expandable sleeve 146 (shown in FIG. 7B). In order to facilitate expansion, expandable sleeve 146 includes a longitudinal slit 154 in at least a distal extremity thereof. When outer shaft 144 is retracted relative to sleeve 146, sleeve 146 may be controllably expanded by axially twisting sleeve 146 such that the opposing edges 156 along longitudinal slit 154 pivot away from one another, forming a cone shape (FIG. 7B). In this way, the expansion of stents 152 is further controllable after retraction of outer shaft 144 by controlling the rate of twisting of sleeve 146. An actuator may be provided at the proximal end of delivery catheter 142 to control such twisting. Optionally, sleeve 146 may have a helical thread on its outer surface that mates with a complementary thread on the interior of outer shaft 144 such that sleeve 146 is automatically twisted as outer shaft 144 is retracted. As in the embodiment of FIGS. 6A-C, following stent deployment, sleeve 146 is retracted from the space between the deployed stents and the vessel wall and returned within outer shaft 144. Sleeve 146 may be resiliently biased to return to its unexpanded configuration, or may be manually twisted back to an unexpanded shape by the operator.

In another embodiment, shown in FIGS. 8A-C, delivery catheter 160 is again constructed much like delivery catheter 129 of FIGS. 6A-C, including an outer shaft 162, a slidable expandable sleeve 164 carrying stents 166, a pusher shaft 168, and an inner shaft 170. A nosecone 172 is attached to the distal end of inner shaft 170 and has a concavity 174 at its proximal end configured to receive the distal end of sleeve 164. A distal extremity of sleeve 164 includes a plurality of axial slits 176 defining separate deflectable longitudinal beams 178. Sleeve 164 includes at least two, preferably four, and as many as six, eight, or more slits 176 to provide a corresponding number of longitudinal beams 178. Longitudinal beams 178 are resiliently biased into an axial orientation wherein sleeve 164 is generally cylindrical. Longitudinal beams 178 have sufficient stiffness against lateral deflection to resist and control the expansion of stents 166.

Advantageously, by containing the distal ends of longitudinal beams 178 in concavity 174, outer shaft 162 may be retracted to expose the desired number of stents to cover a target lesion without immediate expansion of stents 166, as shown in FIG. 8B. When the desired number of stents 166 is exposed, inner shaft 170 may be advanced distally relative to sleeve 164, releasing longitudinal beams 178 from concavity 174. This permits longitudinal beams 178 to laterally deflect, allowing stents 166 to expand, as shown in FIG. 8C. When full expansion is achieved, longitudinal beams 178 may be retracted from between stents 166 and the vessel wall. Longitudinal beams 178 then return to their undeflected axial orientation, allowing inner shaft 170 to be retracted so as to return the distal ends of longitudinal beams 178 into concavity 174. Inner shaft 170 and sleeve 164 may then be retracted into outer shaft 162 while maintaining pressure on pusher shaft 168, thereby advancing additional stents 166 toward the distal end of sleeve 164 for additional deployments.

In some embodiments of the stent delivery catheter of the invention, the stents themselves are configured to provide greater control and precision in stent deployment. For example, FIGS. 9A-9B illustrates a delivery catheter 180 having a plurality of stents 182 disposed in an outer shaft 184. An inner shaft 186 with optional balloon 188 and nosecone 190 extends through outer shaft 184 and stents 182 and is axially movable relative thereto. A pusher shaft (not shown) is slidably disposed over inner shaft 186 and engages stents 182 for purposes of deploying stents 182 from outer shaft 186 and repositioning the remaining stents 182 within outer shaft 186, as in earlier embodiments. In this embodiment, stents 182 comprise a plurality of struts 191 forming a series of rings 192 interconnected at joints 193. Each ring 192 has a series of closed cells 194 interconnected circumferentially and having an "I" shape in the unexpanded configuration.

As outer shaft 184 is retracted to deploy one or more stents 182, at least a distal ring 192' is configured to expand into engagement with the vessel wall before the entire length of the stent 182 is deployed from outer shaft 184 (FIG. 9A). Once in engagement with the lesion L in vessel V, distal ring 192' anchors stent 182 in position as the remainder of the stent is deployed (FIG. 9B), preventing "watermelon seeding" of the stent from the catheter. The axial length of stent 182, the length of each ring 192, the number of rings, the stiffness of struts 191, and the flexibility of joints 193 are all selected to optimize this deployment behavior. Each stent 182 has at least two, and preferably four or more rings 192, each ring being about 2-5 mm in length, giving stent 182 an overall length of at least about 8-20 mm. Of course, stents of shorter or longer length are also contemplated within the scope of the invention. Lesions longer than each stent 182 may be treated by deploying multiple stents 182 end-to-end. Advantageously, each stent 182 can be deployed precisely at a desired spacing from a previously-deployed stent 182 because the distal ring 192' of each stent 182 can be first allowed to expand into engagement with the vessel at the target location, anchoring the stent in position as the remainder is deployed.

Rings 192 are preferably formed from a common piece of material and are integrally interconnected at joints 193, making joints 193 relatively rigid. In this embodiment, the majority of flexibility between rings 192 is provided by struts 191 rather than by joints 193. Alternatively, joints 193 may comprise welded connections between rings 192 which are also fairly rigid. As a further alternative, joints 193 may comprise hinge or spring structures to allow greater deflection between adjacent rings 192, as exemplified in FIGS. 10A-10B, described below.

In the embodiment of FIG. 10A-10B, stents 200 are constructed similarly to stents 182 of FIGS. 9A-9B, including a plurality of interconnected rings 202 having I-shaped cells 204. However, in this embodiment, some of rings 202 are interconnected by spring members 206 that may be elongated to increase the distance between rings 202 and that are resiliently biased into a shortened configuration to draw rings 202 toward each other. In one embodiment, spring members 206 have a wave-like shape and extend from the tip of an axial projection 208 on one ring 202 to a concave portion 210 between axial projections 208 on the adjacent ring 202. Of course a variety of spring configurations and connection locations are possible, including zig-zags, coils, spirals, accordion or telescoping structures, and the like. Further, resilient elongatable elastomeric elements may link the adjacent rings 202. In the illustrated embodiment, stent 200 comprises two pairs of rings 202, with the rings of each pair interconnected by integral joints 212 as in FIGS. 9A-B and the pairs of rings 202 being connected to each other by spring members 206. Stents 200 may alternatively include two, three, five, six or more rings 202, and spring members 206 may interconnect all or only a portion of rings 202.

Spring members 206 may be formed of the same or different material as that of rings 202, depending upon the desired performance characteristics. In addition, spring members 206 may be biodegradable so as to erode and eventually disappear, leaving the adjacent pairs of rings 202 unconnected.

During deployment, as outer shaft 184 is retracted to expose a stent 200, the distal pair of rings 202' first expands into engagement with lesion L in vessel V (FIG. 10A). Spring members 206 elongate to allow rings 202' to fully expand without pulling the second pair of rings 202" from outer shaft 184. As retraction of outer shaft 184 continues, the second pair of rings 202" expands and simultaneously is drawn toward distal ring pair 182' by contraction of spring members 206 (FIG. 10B). This results in a predictable and constant axial spacing between the adjacent pairs of rings 202. In addition, spring members 206 maintain rotational alignment of rings 202 to maintain the interleaving of axial projections 208 without overlap. As in previous embodiments, multiple stents 200 may be deployed sequentially from delivery catheter 180 to cover longer lesions. The ability to precisely deploy each stent permits the relative axial spacing and rotational position of such stents to be controlled to avoid excessive space or overlap.

In a further embodiment, shown schematically in FIGS. 11A-11C, a delivery catheter 216 has an outer shaft 218 carrying a plurality of stents 220. An inner shaft 222 extends through outer shaft 218 to a nosecone 224, and a pusher shaft 226 is slidably disposed over inner shaft 222. An anchoring balloon 228 is mounted to inner shaft 222 proximal to nosecone 224. Anchoring balloon 228 has an axial length sufficient to frictionally engage the wall of vessel V and remain stable so as to anchor delivery catheter 216 in place as further described below. Preferably, anchoring balloon 228 has a length about equal to the length of one of stents 220.

In use, outer shaft 218 is retracted so that a first stent 220' is released therefrom and expands into engagement with lesion L (FIG. 11A). Anchoring balloon 228 is then inflated until it engages the interior of stent 220' (FIG. 11B). This not only stabilizes delivery catheter 216, but may be used to further expand stent 220' and/or dilate lesion L to firmly implant stent 220'. While keeping anchoring balloon inflated within stent 220', outer shaft 218 is further retracted to release a second stent 220", which expands into engagement with lesion L (FIG. 11C). Advantageously, anchoring balloon 228 stabilizes delivery catheter 216 and anchors it in position relative to first stent 220' as second stent 220" is deployed. Second stent 220" is thus deployable precisely at the intended spacing and rotational position relative to first stent 220'. Anchoring balloon 228 may then be deflated and retracted into outer shaft 218, with pressure maintained upon pusher shaft 226 to reposition remaining stents 220 at the distal end of inner shaft 222.

FIGS. 11D-11F illustrate another embodiment of a delivery catheter 219 in which a plurality of self-expanding stents 221 are slidably disposed over an elongated balloon 223. Balloon 223 preferably has a length as long as the longest lesion that is to be treated with the device, e.g. 50-200 mm. A pusher 225 is slidable relative to balloon 223 and has a tubular distal portion 227 disposed over balloon 223 which engages the proximal-most stent 221P. A sheath 229 is slidably disposed over pusher 225, stents 221 and balloon 223 and maintains stents 221 in a radially contracted configuration. In this embodiment, moderate pressure is maintained within balloon 223 during deployment of stents 221 so that the balloon expands simultaneously with each stent. As shown in FIG. 11B, as sheath 229 is retracted, a first stent 221A and a distal portion of balloon 223 are exposed. By maintaining moderate inflation pressure in balloon 223 as sheath 220 is retracted the exposed portion of balloon 223 expands with the first stent 221A, inhibiting distal migration of the stent from delivery catheter 219. One or more additional stents 221 may be deployed by further retraction of sheath 229, during which balloon 223 remains expanded within first stent 221 anchoring the delivery catheter 219 in position (not shown). As each additional stent is exposed from sheath 229, the pressure in balloon 223 causes it to expand with the stent so as to control its rotational and axial position. Of course, stents 221 may have any of a variety of different configurations, including having open or closed cells, zig-zag or wave-shaped struts, and/or axially interleaving elements as described above.

Figure 13A:
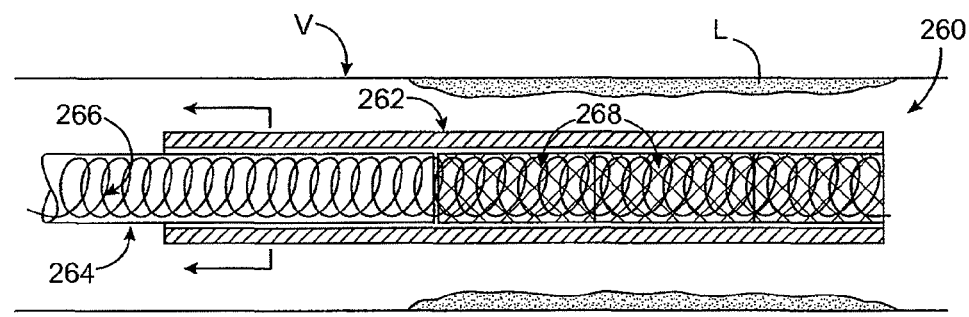
FIGS. 13A-13C are side cross-sectional views of a distal portion of a prosthesis delivery catheter according to another embodiment of the invention, demonstrating a method for delivering prostheses in a vessel.
Figure 13B:
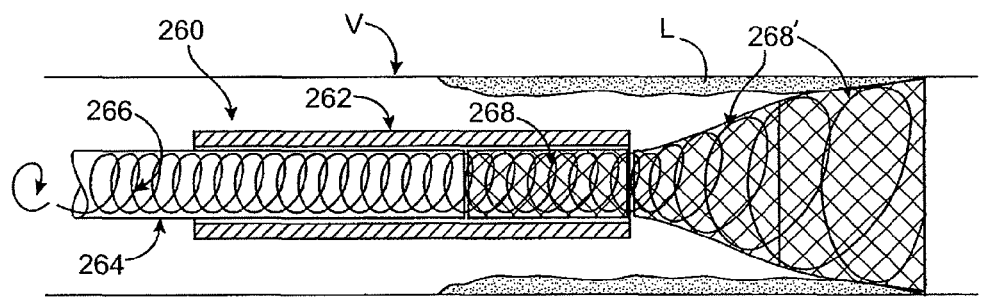
Figure 13C:
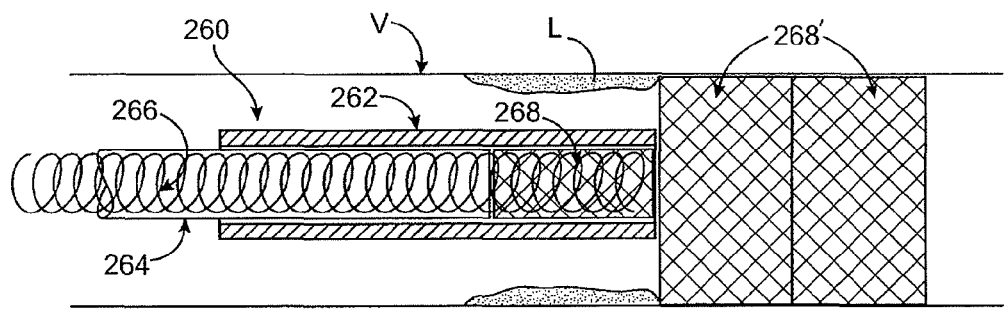

In FIG. 13A, delivery catheter 260 is positioned adjacent a lesion L in a vessel V. Outer shaft 262 may then be retracted (solid-tipped arrows) to begin deployment of stents 268. In FIG. 13B, outer shaft 262 has been retracted to expose two stents 268', thus allowing them to expand within the vessel V. Coil 266 expands along with expanding stents 268' and remains coupled with them, thus helping prevent axial displacement ("watermelon seeding") and in some cases rotation of stents 268' relative to one another. Once stents 268' have been exposed, and stents 268' and coil 266 have expanded so that at least a distal portion of the distal-most stent 268' is contacting the vessel wall, coil 266 is withdrawn from expanded stents 268'. This may be accomplished, in one embodiment, by rotating coil 266 (as shown by the solid-tipped arrow) to unscrew coil 266 from stents 268'. Alternatively, coil 266 may be configured to be simply pulled proximally without rotation to decouple it from stents 268'. Preferably, coil 266 has a radiopaque marker at its distal tip and/or at other suitable locations along its length to allow visualization via fluoroscopy. To facilitate retraction of coil 266 from stents 268', coil 266 may be coated or covered with a lubricious or other friction-reducing coating or sleeve. Rotation is continued to retract coil 266 back into outer shaft 262 and the remaining unexpanded stents 268. In FIG. 13C, coil 266 has been retracted out of expanded stents 268', thus allowing them to fully expand into contact with the inner surface of the vessel V. The process just described may be repeated as many times as desired to treat a long lesion L and/or multiple lesions L.

Optionally, balloon 223 may have surface features or coatings on its periphery that enhance retention of stents 221 thereon. Such features may include structures such as scales or protuberances that are activated by pressurization of the balloon so that retention is lessened when the balloon is deflated, but heightened when the balloon is pressurized. Following stent deployment, pressure can optionally be increased in balloon 223 for post-dilation of stents 221 and the target lesion L. Balloon 223 is then deflated and retracted within sheath 229 as distal pressure is maintained against pusher 225, repositioning stents 221 near the distal end of balloon 223 within sheath 229 for deployment at another location, as shown in FIG. 11C.

Figure 12:
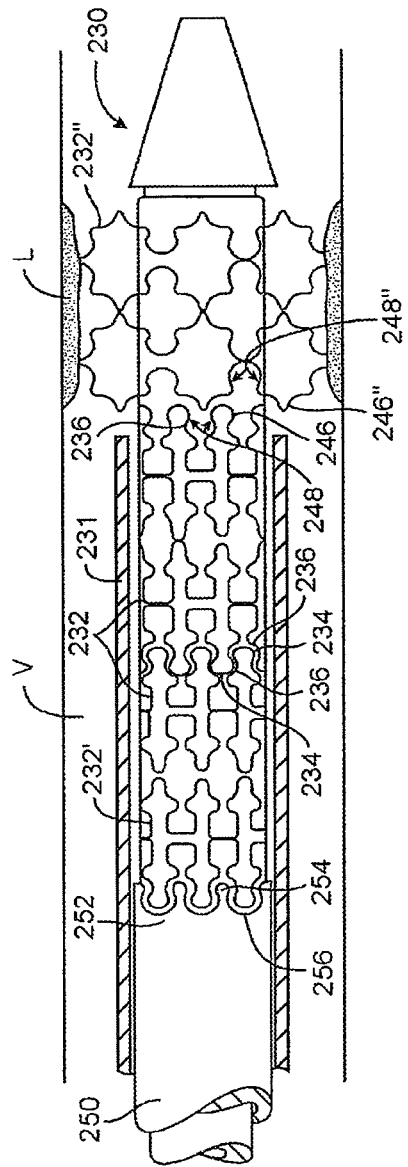
FIG. 12 is a side cross-sectional view of a distal portion of a prosthesis delivery catheter in a vessel according to the invention in still another embodiment thereof, showing a first prosthesis deployed in a lesion.

In a further embodiment, the stents in the delivery catheter of the invention may releasably interconnect with one another and/or with the pusher shaft to enable greater control and precision during deployment. As illustrated in FIG. 12, delivery catheter 230 carries a plurality of stents 232 having a structure much like that described above in connection with FIGS. 9A-9B. However, in this embodiment, the axial projections 234 extending distally and proximally from stents 232 are configured to interconnect with concavities 236 on adjacent stents 232 until expanded. In one embodiment, axial projections 234 have enlarged heads 246 and concavities 236 have necks 248 that retain heads 246 within concavities 236 in the unexpanded configuration. Pusher shaft 250 has a distal end 252 having projections 254 and concavities 256 like those of stents 232, thus being able to interconnect with the proximal-most stent 232'. When a stent 232" expands, the interconnecting structures thereon are configured to separate from the adjacent stent or pusher shaft, thus releasing the deployed stent 232" from delivery catheter 230. In the example shown, as stent 232" expands, heads 246" contract in size while necks 248" enlarge, thereby allowing heads 246" on the expanded stent to be released from concavities 236 in the adjacent unexpanded stent, and vice versa. By exerting traction on pusher shaft 250 during the deployment process, the line of stents 232 is kept from moving distally relative to outer shaft 231, thus preventing the deployed stent 232" from "watermelon seeding" as it expands.

Various types of interconnecting structures between adjacent stents and between the stents and the pusher shaft are possible within the scope of the invention, including those described in co-pending application Ser. No. 10/738,666, filed Dec. 16, 2003, which is incorporated herein by reference. Such interconnecting structures may also be breakable or frangible to facilitate separation as the stent expands. In addition, a mechanism such as an expandable balloon or cutting device may be disposed at the distal end of delivery catheter 230 to assist in separating stents 232 upon deployment. Further, the interconnections between stents may be different than the interconnection between the proximal-most stent and the pusher shaft. For example, the pusher shaft may have hooks, magnets, or other mechanisms suitable for releasably holding and maintaining traction on the proximal end of a stent until it is deployed.

In another embodiment, as shown in FIGS. 13A-13C, a delivery catheter 260 includes an outer shaft 262 (or sheath), a pusher shaft 264 slidably disposed within outer shaft 262, a plurality of stents 268 slidably disposed within outer shaft 262, and a coil 266 extending through catheter 260 and coupled with stents 268. In various embodiments, coil 266 may extend through pusher shaft 264 (as shown) or be disposed around pusher shaft 264. Coil 268 is constructed of a resilient material, such as but not limited to Nitinol™, spring stainless steel, resilient polymers, or other shape memory or super-elastic materials. Coil 266 may have various pitches, depending upon the desired spacing between adjacent loops. Coil 266 may have a relatively high pitch (individual loops spread relatively far apart), e.g., between about 2 and 6 loops disposed in each stent 268. In other embodiments, coil 266 may have a lower pitch (individual loops closer together), e.g., greater than 6 loops, or even greater than 10 loops disposed in each stent 268. Of course, the number of loops will vary according to the length of each stent 268, the thickness, diameter, and flexibility of coil 266, and other factors. Adjacent loops in coil 266 may also be in contact with each other to form a tube having a substantially continuous wall without openings. Coupling of coil 266 with stents 268 is described further below with reference to FIGS. 14-16.

In FIG. 13A, delivery catheter 260 is positioned adjacent a lesion L in a vessel V. Outer shaft 262 may then be retracted (solid-tipped arrows) to begin deployment of stents 268. In FIG. 13B, outer shaft 262 has been retracted to expose two stents 268', thus allowing them to expand within the vessel V. Coil 266 expands along with expanding stents 268' and remains coupled with them, thus helping prevent axial displacement ("watermelon seeding") and in some cases rotation of stents 268' relative to one another. Once stents 268' have been exposed, and stents 268' and coil 266 have expanded so that at least a distal portion of the distal-most stent 268' is contacting the vessel wall, coil 266 is withdrawn from expanded stents 268'. This may be accomplished, in one embodiment, by rotating coil 266 (as shown by the solid-tipped arrow) to unscrew coil 266 from stents 268'. To facilitate retraction of coil 266 from stents 268', coil 266 may be coated or covered with a lubricious or other friction-reducing coating or sleeve. Rotation is continued to retract coil 266 back into outer shaft 262 and the remaining unexpanded stents 268. In FIG. 13C, coil 266 has been retracted out of expanded stents 268', thus allowing them to fully expand into contact with the inner surface of the vessel V. The process just described may be repeated as many times as desired to treat a long lesion L and/or multiple lesions L.

In a preferred embodiment, adjacent stents are "keyed," or "interleaved," to each other, meaning that fingers or other protrusions on each end of one stent interleave with complementary fingers/protrusions on immediately adjacent stents, as described above in reference to FIGS. 2A-B, 4B, 9A-B, 10A-B and 12. This feature helps prevent stents from rotating relative to one another during deployment. Optionally, the distal end of the pusher shaft may also include fingers/protrusions to interleave with the proximal end of the proximal-most stent, as shown in FIG. 12 above. Interleaving the stents with the pusher shaft helps prevent rotation of the stents relative to the outer shaft.

Referring to FIG. 14, a stent 270 is shown in side view with a portion of a coil 272 coupled therewith. In some embodiments, coil 272 is threaded though openings 274 between struts 275 in stent 270. This is shown in end-on cross section, in FIG. 15. As described above, coil 272 may be made of any of a number of resilient materials and may have a variety of different configurations in various embodiments. For example, coil 272 is shown having four loops for one stent 270, whereas in alternative embodiments fewer or more loops per stent may be used. In an alternative embodiment (not shown), coil 272 may be disposed around the outside stents 270, with stents 270 being capable of sliding axially through coil 272 or being helically (screw) driven by rotating coil 272.

FIG. 16 shows and end-on view of another embodiment of a stent 280 coupled with a coil 282. In this embodiment, stent 280 includes multiple, inwardly-bent struts 284, through which coil 282 is threaded. Thus, coil 282 is disposed entirely within the inner diameter of stent 280. Such struts 284 may be adapted to remain in the inwardly-bent configuration only when stent 280 is collapsed in the catheter, such that struts 284 return to a position even with the cylindrical surface of stent 280 when stent 280 expands. Alternatively, struts 284 may remain in the inwardly bent configuration even when stents 280 expand. Or struts 284 may be merely elastically deflected to the inwardly bent configuration to facilitate threading coil 282 therethrough, with struts 284 being biased to return to a position along the cylindrical surface of stent 280 when coil 282 is removed.

In another embodiment, illustrated in FIG. 17, a delivery catheter 290 includes a tubular outer shaft 292 and a tubular inner shaft 294 slidably disposed in outer shaft 202. An evertible tube 295 is attached to the distal end of inner shaft 294 and extends distally therefrom. Evertible tube 295 has a flexible distal portion 295' configured to evert (fold over on itself), and a distal end 297 attached to the distal end of outer shaft 292. To provide flexibility, at least the flexible distal portion 295' of evertible tube 295 (and optionally all of evertible tube 295) may be made of a flexible polymer or other bendable material and may, in some embodiments, have thinner walls than inner shaft 294 or outer shaft 292. A pusher shaft 300 is slidably disposed in inner shaft 294, and a plurality of stents 302 are slidably disposed within inner shaft 294 distally of pusher shaft 300. When outer shaft 292 is retracted (slid proximally) relative to inner shaft 294, the flexible distal portion 295' of evertible tube 295 everts (i.e., bends outward and folds back on itself) and thus follows outer shaft 292 proximally. This process of sliding outer shaft 292 proximally to evert and pull flexible distal portion 295' proximally causes stents 302' to deploy out of the distal end 299 of the delivery catheter 290.

Axial displacement of each stent 302' is controlled (and watermelon seeding is avoided) due to frictional engagement with the inner surface 296 of evertible tube 295. To enhance retention of stents 302 in evertible tube 295, inner surface 296 may include adherent coatings or other surface features adapted to engage and retain stents 302. For example, inner surface 296 may comprise a layer or coating of sticky, tacky or otherwise high-friction material. Alternatively, inner surface 296 may include friction-inducing features such as roughened areas, bumps, spines, bristles, ridges, ribs, channels, grooves, or random surface irregularities. As flexible distal portion 294' everts and moves proximally, stents 302' peel off of adherent surface 296 in a controlled fashion.

In an alternative embodiment, shown in FIG. 18, stents 308 are partially embedded in an inner surface 306 of an evertible tube 304. For example, evertible tube 304 may have an inner surface 306 that softens and/or becomes malleable when heated. When stents 308 are loaded in evertible tube 304, inner surface 306 is heated so that stents 308 are partially and releasably embedded in inner surface 306, with portions of the softened surface material extending through the openings 307 between struts 309 in stent 308. To deploy stents 308, the distal end of evertible tube 304 is everted as described above, peeling inner surface 306 away from each stent 308 to release it into the vessel. Because stents 308 are embedded in inner surface 306, they are not fully released from the catheter until evertible tube 304 is peeled completely off of stent 308, at which time the distal end of stent 308 has expanded into contact with the vessel. Uncontrolled axial displacement of stent 308 is thus avoided.

In the embodiment shown in FIG. 19, an evertible tube 314 includes multiple retention structures 316 on an inner surface 319, which extend through openings 317 between struts 315 in a stent 318 to releasably hold stent 318. Retention structures 316 are preferably adapted to extend through openings 317 and abut the inner surfaces of struts 315 to provide secure but releasable engagement with stents 318. When the distal end of evertible tube 314 is peeled back to deploy stents 318, retention structures 316 are adapted to be pulled out of openings 317 to release stent 318. Retention structures 316 may comprise, for example, multiple mushroom-shaped protrusions (as shown) or alternatively, or alternatively, L-shaped, T-shaped, barbed, pyramidal, arrow-shaped, linear or hook-shaped protrusions.

Retention structures 316 may be integrally formed with evertible tube 314 and made of the same flexible polymer, or alternatively may be separate structures of polymer, metal wire or other flexible material attached to evertible tube 314. Such retention structures may be positioned to engage stent 318 at various locations along its length, e.g. at several locations along the entire length of the stent, e.g. near the proximal and distal ends (as shown), only near the proximal end, only near the distal end, only at the middle, or at another discreet location.

Referring now to FIGS. 20-23, a further embodiment of a prosthesis delivery catheter according to the invention will be described. In this embodiment, delivery catheter 400 has a tubular outer shaft 402, a pusher shaft 404 slidably disposed within outer shaft 402, and an inner shaft 406 slidably disposed within pusher shaft 402. Inner shaft 406 has a guidewire lumen extending axially therethrough for receiving a guidewire GW. A plurality of self-expanding stents 420 (not shown in FIG. 20A) are slidably disposed within outer shaft 402 distally of pusher shaft 404, which can be used to exert a distal force against such stents for the deployment thereof, as described further below. A nosecone 407 is fixed to the distal end of inner shaft 406 and has a proximally-facing aperture 409 in its proximal end. Outer shaft 402 has a distal end 408 to which is attached a control member 410 defining an interior 411 in which a stent 420 may be received. Control member 410 has a plurality of flexible tines 412 extending distally and having free distal ends 414 removably received within aperture 409. A wall 416 extending circumferentially around aperture 409 retains flexible tines 412 within aperture 409. Nosecone 407 is movable distally relative to control member 410 to release tines 412 from aperture 409.

Control member 410 may be constructed of a polymer, metal, or other flexible and resilient material. Tines 412 are deflectable outwardly under the expansion force of stents 420. Tines 412 are preferably biased inwardly into general alignment with the longitudinal axis of delivery catheter 400 such that free distal ends 414 remain positioned inwardly near inner shaft 406 even after release from aperture 409. Tines 412 may include a friction-enhancing coating, texture, cover, or other surface features on their inwardly-facing surfaces to create more friction with stents 420. Alternatively, a lubricious coating may be provided on the inner or outer surfaces of tines 412 for greater slidability. Tines 412 may have an axial length which is less than or equal to the length of one stent 420, a length greater than the length of one stent 420, or a length as long as the length of 2, 3 or more stents 420. Aperture 409 may be relatively shallow, as shown, so as to receive only the free distal ends 414 of tines 412, or may be somewhat deeper so that a portion or substantially all of the length of tines 412 is disposed within aperture 409.

Figure 21D:
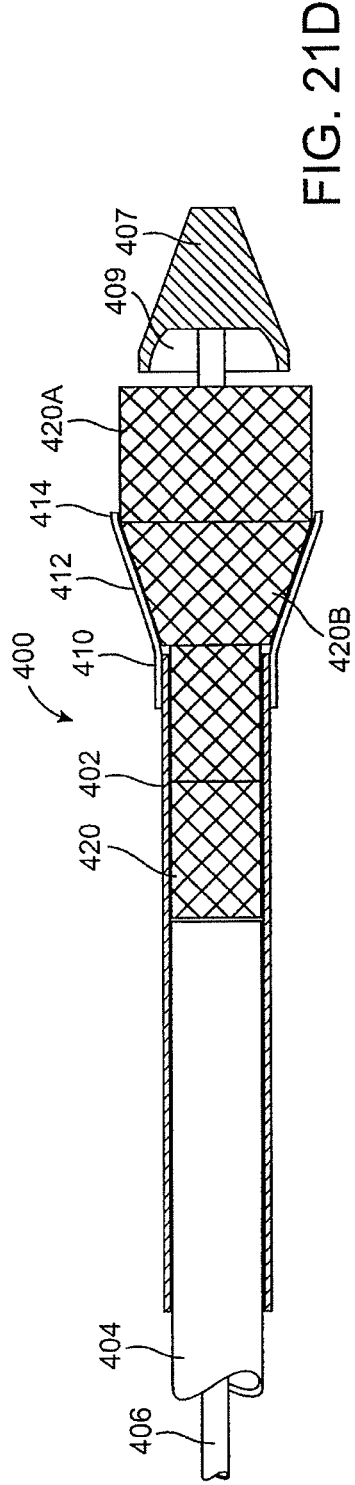
Figure 21E:
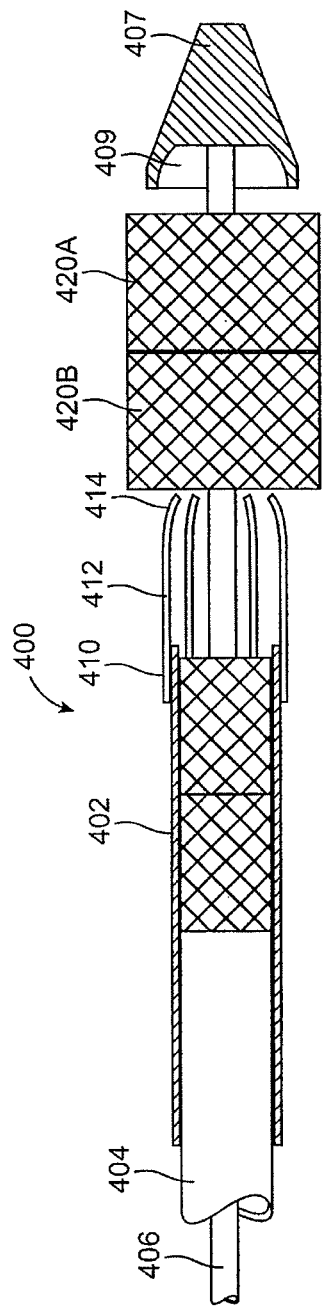

As shown in FIGS. 21A-21E, in use, delivery catheter 400 is positioned in a vessel at the treatment site with tines 412 disposed within aperture 409 on nosecone 407. Nosecone 407 is then advanced distally relative to control member 410 (or outer shaft 402 is retracted proximally relative to nosecone 407) to release tines 412 from aperture 409 as shown in FIG. 21B. Outer shaft 402 is then retracted relative to pusher shaft 404 (or pusher shaft 404 may be pushed distally) to advance one or more stents 420 out of outer shaft 402 into control member 410, as shown in FIG. 21C. Tines 412 exert an inward force on stents 420 to resist, but not prevent, the expansion thereof. This slows down the rate of stent expansion and also provides frictional resistance between tines 412 and the outer surface of stent 420, thereby reducing the tendency of the stent to jump distally as it expands. As shown in FIG. 21D, tines 412 preferably have a length selected so that before a first stent 420A is fully expanded and released from control member 410, a second stent 420B is at least partially contained within control member 410. In this way multiple stents 420 may be deployed end-to-end with a desired degree of inter-stent spacing and without overlaps or excessive gaps. Outer shaft 402 is retracted until the desired number of stents 420 has been deployed at the treatment site. Outer shaft 402 and pusher shaft 404 are then retracted together to slidably decouple tines 412 from the deployed stents 420, as shown in FIG. 21E. Nosecone 407 may then be retracted through the deployed stents until tines 412 are positioned in aperture 409. The device can then be repositioned at a new treatment site for additional deployments.

Figure 22:
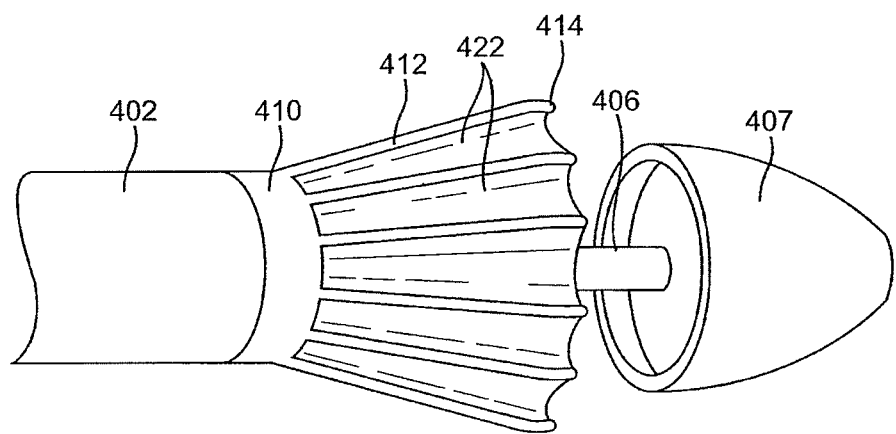
FIG. 22 is an oblique view of a distal end of a prosthesis delivery catheter according to the invention in a further embodiment thereof.

FIG. 22 illustrates an alternative embodiment of control member 410, in which multiple webs 422 are disposed between tines 412. Webs 422 are preferably made of a flexible, resilient and distensible elastomer configured to radially expand or stretch under the expansion force of a stent 420. Webs 422 may comprise a substantially continuous, non-porous sheet, or may have openings, or may be comprised of a plurality of woven strands. Optionally, webs 422 may extend over the outer and/or inner surfaces of tines 412, and may connect to form a continuous tubular structure. Webs 422 may serve to provide additional resistance to stent expansion, may provide a protective surface around stent 420 and/or tines 412, and may also have lubricity on their outer and/or inner surfaces to facilitate withdrawal of tines 412 from stents 420 following deployment.

Figure 23:
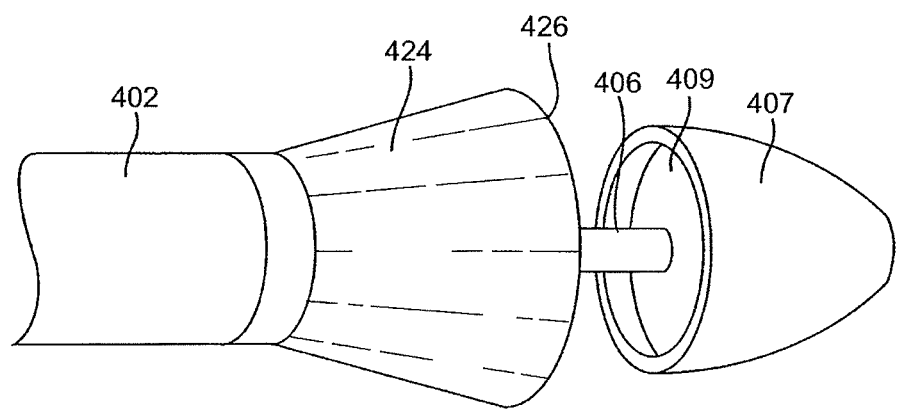
FIG. 23 is an oblique view of a distal end of a prosthesis delivery catheter according to the invention in still another embodiment thereof.

FIG. 23 illustrates a further embodiment in which control member 410 comprises a single distensible tubular member 424 rather than having tines 412. Tubular member 424 is preferably a flexible, resilient, and distensible elastomer configured to stretch or expand radially under the expansion force of a stent 420. Tubular member 424 is normally in a radially contracted, generally cylindrical shape without stents 420 positioned therein, with its distal end 426 adapted for positioning in aperture 409 in nosecone 407. As with web 422, tubular member 424 may be a substantially continuous, non-porous sheet, or it may have openings, or it may be comprised of a plurality of woven strands. In addition, tubular member 424 may have a lubricious outer or inner surface to facilitate withdrawal from stents 420 following deployment. The inner surface of tubular member 424 may also include friction enhancing coatings, textures, or features to enhance retention of stents 420 therein.

While the above is a complete description of the preferred embodiments of the invention, various alternatives, modifications, improvements and additions are possible without departing from the scope thereof, which is defined by the claims.

What is claimed is:

1. A prosthesis delivery catheter for delivering a prosthesis into a vessel, said catheter comprising:
    an outer shaft having a distal end, a first lumen, and a substantially inexpandable outer diameter, the outer shaft defining a lumen space;
    a plurality of self-expanding tubular prostheses having a contracted configuration and a radially expanded configuration with an expanded diameter adapted to contact the vessel, the prostheses carried within the first lumen and being adapted to radially expand into the expanded configuration upon deployment from the first lumen, wherein adjacent self-expanding prostheses are unconnected and free of material deployable with the prostheses extending therebetween thereby allowing axial separation of one prosthesis from an adjacent prosthesis in the contracted configuration; and
    a control member comprising a plurality of tines arranged in a cylindrical pattern and extending distally from the distal end of the outer shaft and defining an interior communicating with the first lumen for receiving one or more of the prostheses when the prostheses are advanced distally, the tines having an undeflected shape when not engaged by any of the prostheses and each of the tines comprising a straight portion and an arcuate distal tip that is biased radially inward in the undeflected shape so that the arcuate distal tip protrudes into the lumen space, wherein the tines deflect radially outwardly under expansion force imparted by a first prosthesis to at least the expanded diameter of the prostheses when engaged by the first prosthesis during the expansion thereof and resiliently return to the undeflected shape when the first prosthesis is removed from the interior;
    wherein the control member further comprises a web extending between the tines and the web is a distensible elastomer.

2. The prosthesis delivery catheter of claim 1, wherein a proximal end of the control member is disposed over and coupled with an outer surface of the outer shaft proximal to a distal end of the outer shaft.

3. The prosthesis delivery catheter of claim 1, further comprising:
    an inner shaft slidable relative to the outer shaft; and
    a nose piece at the distal end of the inner shaft disposed distally of the control member, the nose piece having a proximal chamber adapted to receive a distal end of the control member, the proximal chamber having an arcuate surface corresponding to the arcuate distal tip.

4. The prosthesis delivery catheter of claim 3, wherein the distal tips are positionable in the proximal chamber of the nose piece before being engaged by the first prosthesis and after the first prosthesis is removed from the interior.

5. The prosthesis delivery catheter of claim 1, wherein the control member is adapted to be slidably removed from the prosthesis following the expansion thereof.

6. The prosthesis delivery catheter of claim 1, wherein the prostheses are adapted for deployment in groups of at least two at a single treatment site.

7. The prosthesis delivery catheter of claim 6, wherein each of the prostheses has axially extending elements configured to interleave with axially extending elements on an adjacent prosthesis.

8. The prosthesis delivery catheter of claim 7, wherein the control member is adapted to control expansion of the prostheses such that the axially extending elements remain interleaved when at least two prostheses are deployed adjacent to each other.

9. The prosthesis delivery catheter of claim 1, further comprising a pusher slidably disposed within the first lumen, the pusher engaging at least one of the prostheses to deploy the prostheses from the first lumen.

10. A prosthesis delivery catheter for delivering a prosthesis into a vessel, said catheter comprising:
 an outer shaft having a distal end and a first lumen, the outer shaft defining a lumen space;
 a plurality of self-expanding tubular prostheses having a contracted configuration and a radially expanded configuration with an expanded diameter adapted to contact the vessel, the prostheses carried within the first lumen and being adapted to radially expand into the expanded configuration upon deployment from the first lumen, wherein a first prosthesis is axially separable from an adjacent prosthesis in the contracted configuration; and
 a control member comprising a plurality of tines arranged in a cylindrical pattern and extending distally from the distal end of the outer shaft and defining an interior communicating with the first lumen for receiving one or more of the prostheses when the prostheses are advanced distally, the control member having an undeflected shape when not engaged by any of the prostheses and each of the tines comprising a straight portion and an arcuate distal tip that is biased radially inward in the undeflected shape so that the arcuate distal tip protrudes into the lumen space, the tines being configured to deflect radially outwardly to at least the expanded diameter of the prostheses when engaged by a prosthesis during the expansion thereof, the control member being configured to resiliently return to the undeflected shape when the prosthesis is removed from the interior, and
 wherein the control member further comprises a web extending between the tines.

11. The prosthesis delivery catheter of claim 10, wherein the web is a distensible elastomer.

12. A prosthesis delivery catheter for delivering a prosthesis into a vessel, said catheter comprising:
 an outer shaft having a distal end a first lumen, and a substantially inexpandable outer diameter, the outer shaft defining a lumen space;
 a plurality of self-expanding tubular prostheses having a contracted configuration and a radially expanded configuration with an expanded diameter adapted to contact the vessel, the prostheses carried within the first lumen and being adapted to radially expand into the expanded configuration upon deployment from the first lumen, wherein adjacent self-expanding prostheses are unconnected and free of material deployable with the prostheses extending therebetween thereby allowing axial separation of one prosthesis from an adjacent prosthesis in the contracted configuration; and
 a control member comprising a plurality of tines arranged in a cylindrical pattern and extending distally from the distal end of the outer shaft and defining an interior communicating with the first lumen for receiving one or more of the prostheses when the prostheses are advanced distally, and having an undeflected shape when not engaged by any of the prostheses, wherein each tine comprises a straight portion and an arcuate distal tip that is biased radially inward in the undeflected shape so that the arcuate distal tip protrudes into the lumen space, the tines being configured to deflect radially outwardly under expansion force imparted by a first prosthesis from the undeflected shape to at least the expanded diameter of the prostheses when engaged by the first prosthesis during the expansion thereof, the tines maintaining engagement with each prosthesis until it expands into contact with the vessel wall and being configured to resiliently return to the undeflected shape when the prosthesis is removed from the interior;
 wherein the control member further comprises a web extending between the tines and the web is a distensible elastomer.

13. The prosthesis delivery catheter of claim 12, wherein a proximal end of the control member is disposed over and coupled with an outer surface of the outer shaft proximal to a distal end of the outer shaft.

14. The prosthesis delivery catheter of claim 12, further comprising:
 an inner shaft slidable relative to the outer shaft; and
 a nose piece at the distal end of the inner shaft disposed distally of the control member, the nose piece having a proximal chamber adapted to receive a distal end of the control member, the proximal chamber having an arcuate surface corresponding to the arcuate distal tip.

15. The prosthesis delivery catheter of claim 14, wherein the distal tips are positionable in the proximal chamber of the nose piece before being engaged by the first prosthesis and after the first prosthesis is removed from the interior.

16. The prosthesis delivery catheter of claim 12, wherein the control member is adapted to be slidably removed from the prosthesis following the expansion thereof.

17. The prosthesis delivery catheter of claim 12, wherein the prostheses are adapted for deployment in groups of at least two at a single treatment site.

18. The prosthesis delivery catheter of claim 17, wherein each of the prostheses has axially extending elements configured to interleave with axially extending elements on an adjacent prosthesis.

19. The prosthesis delivery catheter of claim 18, wherein the control member is adapted to control expansion of the prostheses such that the axially extending elements remain interleaved when at least two prostheses are deployed adjacent to each other.

20. The prosthesis delivery catheter of claim 12, further comprising a pusher slidably disposed within the first lumen, the pusher engaging at least one of the prostheses to deploy the prostheses from the first lumen.

* * * * *